(12) United States Patent
Takakura et al.

(10) Patent No.: US 7,144,719 B2
(45) Date of Patent: Dec. 5, 2006

(54) METHOD FOR PRODUCING PROTEASE

(75) Inventors: Hikaru Takakura, Shiga (JP); Mio Morishita, Shiga (JP); Tomoko Shimojo, Kyoto (JP); Kiyozo Asada, Shiga (JP); Ikunoshi Kato, Kyoto (JP)

(73) Assignee: Takara Bio, Inc., Otsu Shiga (JP)

( * ) Notice: Subject to any disclaimer, the term of this patent is extended or adjusted under 35 U.S.C. 154(b) by 70 days.

(21) Appl. No.: 10/888,588

(22) Filed: Jul. 12, 2004

(65) Prior Publication Data

US 2005/0084934 A1 Apr. 21, 2005

Related U.S. Application Data

(62) Division of application No. 10/090,624, filed on Mar. 6, 2002, now Pat. No. 6,783,970, which is a division of application No. 09/445,472, filed as application No. PCT/JP98/02465 on Jun. 4, 1998, now Pat. No. 6,358,726.

(30) Foreign Application Priority Data

Jun. 10, 1997 (JP) .................................. 9-151969

(51) Int. Cl.
  C12N 9/50 (2006.01)
  C12N 9/00 (2006.01)
  C12N 1/20 (2006.01)
  C12N 15/00 (2006.01)
  C07H 21/04 (2006.01)

(52) U.S. Cl. ..................... 435/219; 435/183; 435/212; 435/252.3; 435/320.1; 536/23.2

(58) Field of Classification Search ................ 435/183, 435/212, 219, 252.3, 320.1; 536/23.2
See application file for complete search history.

(56) References Cited

U.S. PATENT DOCUMENTS 5,756,339 A 5/1998 Mitta et al.

FOREIGN PATENT DOCUMENTS

| EP | 0306673 A1 | 3/1989 |
| EP | 0870833 A1 | 10/1998 |
| WO | WO97/21823 | 6/1997 |

OTHER PUBLICATIONS

Stahl et al., "Replacement of the *Bacillus subtilis* Subtilisin Structural Gene with an In Vitro-Derived Deletion Mutation", Journal of Bacteriology, 152:411-418 (May 1984).
Yoshimoto et al., "Cloning and Expression of Subtilisin Amylosachariticus Gene", J. Biochem., 103:1060-1065 (1988).
Nakamura et al., "Nucleotide Sequence of the Subtilisin NAT Gene, apr N, of *Bacillus subtilis* (natto)", Biosci. Biotech. Biochem, 56:1869-1871 (1992).
Asada et al., Accession AAR87009. Hypetthermostable protease. May 10, 1996 (Alignment No. 1).
Robinson et al., A gene from the hyperthermophile *Pyrococcus furiosus* whose deduced product is homologous to members of the prolyl oligopeptidase family of proteases, Gene, 152:103-106 (1995).
Attwood et al., Which craft is best in bioinformatics? *Comput. Chem.*, 2001 25(4)329-339 (2001).
Ponting,C.P., Issues in predicting protein function from sequence. *Brief. Bioinform.*, 2(1)19-29 (Mar. 2001).
Asada et al., Accession AAT08131, (nucleotide to nucleotide alignment) (May 10, 1996).
Asada et al., Accession AAT08131, (amino acid to nucleotide alignment) (May 10, 1996).

*Primary Examiner*—Tekchand Saidha
*Assistant Examiner*—Christian L. Fronda
(74) *Attorney, Agent, or Firm*—Browdy and Neimark, PLLC

(57) ABSTRACT

A hyperthermostable protease having the amino acid sequence represented by the SEQ ID NO:1 of the Sequence Listing or a sequence derived therefrom by deletion, substitution, insertion or addition of one to several amino acid residues, a gene encoding the hyperthermostable protease, and a process for preparing the protease, aiming at providing by genetic engineering techniques a hyperthermophile protease which is advantageous for industrial use.

9 Claims, 7 Drawing Sheets

Fig. 2

```
                   10         20         30         40         50
PFUL        MNKKGLITVLF IAIMLLSVVP VHFVSAETPP VSSENSTTSI LPNQQVVTKE
TCES                        MKRLGAVV LALVLVGLLA GTALAAPVKP VVRNNAVQQK
subtilisin                                                MRGKKVWISL 60         70         80         90        100
PFUL        VSQAALNAIM KGQPNMVLII KTKEGKLEEA EVDTVIMFGS ILDENRVLNM
TCES        NYGLLTPGLF KKVQRMNWNQ KTELEKLGAE YGDRDRAVKV LRLMGAQVKY
subtilisin  LFALALIFTM AFGSTSSAQA AGKSNGEKKY IVGFKQTMST MSAAKKKDVI 110        120        130        140        150
PFUL        LLVKIKPEKV KELNYISSLE KAWLNREVKL SPPIVEKDVK TKEPSLEPKM
TCES        SYKIIPAVAV KIKARDLLLI AGMIDTGYFG NTRVSGIKFI QEDYKVQVDD
subtilisin  SEKGGKVQKQ FKYVDAASAT LNEKAVKELK KDPSVAYVEE DHVAHAYAQS 160        170        180        190        200
PFUL        YNSTWVINAL QFIQEFGYDG SGVVVAVLDT GVDPNHPFLS ITPDGRRKII
TCES        ATSVSQIGAD TWNSLGYDG  SGVVVAIVDT GIDANHPDLK GKVIGWYDAV
subtilisin  VPYGVSQIKA PALHSQGYTG SNMKVAVIDS GIDSSHPDLK VAGGASMVPS 210        220        230        240        250
PFUL        EWKDFTDEGF VDTSFSFSKV VNGTLIINTT FQVASGLTLN ESTGLMEYVV
TCES        NGRSTPYDDQ ----------
subtilisin  ETNPFQDNN- ----------

260        270        280        290        300
PFUL        KTVYVSNVTI GNITSANGIY HFGLLPERYF DLNFDGDQED FYPVLVNST
TCES        ---------- ---------- ---------- ---------- ---------
subtilisin  ---------- ---------- ---------- ---------- ---------
```

Fig. 3

```
              310        320        330        340        350
PFUL       GNGYDIAYVD TDLDYDFTDE VPLGQYNVTY DVAVFSYYYG PLNYVLAEID
TCES       ---------- ---------- ---------- ---------- ----------
subtilisin ---------- ---------- ---------- ---------- ----------

360        370        380        390        400
PFUL       PNGEYAVFGW DGHGHGTHVA GTVAGYDSNN DAWDWLSMYS GEWEVFSRLY
TCES       ---------- -YIGHGTHVA GIVACTGSVN SQ-------- ----------
subtilisin ---------- ---SHGTHVA GTVAA--LNN SI-------- ----------

410        420        430        440        450
PFUL       GWDYTNVTTD TVQGVAPGAQ IMAIRVLRSD GRGSMWDIIE CMTYAATHGA
TCES       ---------- YIGVAPGAK  LVGVKVLGAD GSGSVSTIIA CVDWVVQNKD
subtilisin ---------- GVLGVAPSAS LYAVKVLGAD GSGQYSWIIN GIEWAIANNM 460        470        480        490        500
PFUL       ---DVISMS  LGGNAPYLDG TDPESVAVDE LTEKYGVVEV IAAGNEGPGI
TCES       KYGIRVINLS LGSSQSS-DG TDSISQAVNN AWDA--GIVVC VAAGNSGPNT
subtilisin ---DVINMS  LGGP----SG SAALKAAVDK AVAS-GVVVV AAAGNEGTSG 510        520        530        540        550
PFUL       N--IVGSPGV ATKAITVGAA AVPINGVYV SQALGYPDYY GFYYFPAYTN
TCES       Y--TVGSPAA ASKVITVCAV DSNDN----- ---------- ----------
subtilisin SSSTVGYPGK YPSVIAVGAV DSSNQ----- ---------- ----------

560        570        580        590        600
PFUL       VRIAEFSSRG PRIDGEIKPN VVAPGYGIYS SLEMWIGGAD F----MS
TCES       -IASFSSRG  PTADCRLKPE VVAPGVDIIA PRASGTSMGT PINDYYTKAS
subtilisin --RASFSSVG PELD------ VMAPGVSIQS TLEGNKYGA- -----YN
```

Fig. 4

```
                    610        620        630        640        650
PFUL       GTSMATPHVS GVVALISGA KAEGIYYNPD IIKKVLESGA TWEGDPYTG
TCES       GTSMATPHVS GVAALILQAH PSWTPDKVKT ----ALIETA DIVAPKEIAD
subtilisin GTSMASPHVA GAAALILSKH PNWTNTQVRS ----SLENTT TKL-GDS---

660        670        680        690        700
PFUL       QKYTELDQCH GLVNVTKSWE ILKAINGTTL PIVDHWADKS YSDFAEYLGV
TCES       -----IAYGA GRVNVYKAIK YDDYAKLTFT GSVADKGSAT HTFDVSGATF
subtilisin ------FYYCK GLINVQAAAQ *

710        720        730        740        750
PFUL       DVIRGLYARN SIPDIVEWHI KYVGDTEYRT FEIYATEPWI KPFVSGSVIL
TCES       VTATLYWDTG SSDIDLYLYD PNGNEVDYSY TAYYGFEKVG YYNPTAGTWT 760        770        780        790        800
PFUL       ENNTEFVLRV KYDVEGLEPG LYVGRIIIDD PTTPVIEDEI LNTIVIPEKF
TCES       VKVVSYKGAA NYQVDVVSDG SLSQSGGGNP NPNPNPNPTP TTDTQTFTGS 810        820        830        840        850
PFUL       TPENNYTLTW YDINGPEMVT HHFFTVPEGV DVLYAMTTYW DYGLYRPDGM
TCES       VNDYWDTSDT FTMNVNSGAT KITGDLTFDT SYNDLDLYLY DPNGNLVDRS 860        870        880        890        900
PFUL       FVFPYQLDYL PAAVSNPMPG NWELVWTGFN FAPLYESGFL VRIYGVEITP
TCES       TSSNSYEHVE YANPAPGTWT FLVYAYRTYG WADYQLKAVV YYG*

910        920        930        940        950
PFUL       SVWYINRTYL DTNTEFSIEF NITNIYAPIN ATLIPIGLGT YNASVESVGD
```

Fig. 5

```
PFUL    960              970        980        990        1000
        GEFFFIKGIEV PEGTAELKIR IGNPSVPNSD LDLYLYDSKG NLVALDGNPT

PFUL    1010             1020       1030       1040       1050
        AEEEVVVEYP KPGVYSIVVH GYSVRDENGN PTTTFDLVV QMTLDNGNIK

PFUL    1060             1070       1080       1090       1100
        LDKDSIILGS NESVVVTANI TIDRDHPTGV YSGIIEIRDN EVYQDTNTSI

PFUL    1110             1120       1130       1140       1150
        AKIPITLVID KADFAVGLTP AEGVLGEARN YTLIVKHALT LEPVPNATVI

PFUL    1160             1170       1180       1190       1200
        IGNYTYLTDE NGTVFFTYAP TKLGSDEITV IVKKENFNTL EKTFQITVSE

PFUL    1210             1220       1230       1240       1250
        PEITEEDINE PKLAMSSPEA NATIVSVEME SEGGVKKTVT VEITINGTAN

PFUL    1260             1270       1280       1290       1300
        ETATIVVPVP KKAENIEVSG DHVISYSIEE GEYAKYVIIT VKFASPVTVT

PFUL    1310             1320       1330       1340       1350
        VTYTIYAGPR VSILTLNFLG YSWYRLYSQK FDELYQKALE LGVDNETLAL

PFUL    1360             1370       1380       1390       1400
        ALSYHEKAKE YYEKALELSE GNIIQYLGDI RLLPPLRQAY INEMKAVKIL

PFUL    1410
        EKAIEELEGE E*
```

METHOD FOR PRODUCING PROTEASE

CROSS-REFERENCE TO RELATED APPLICATIONS

The present application is a divisional of application Ser. No. 10/090,624, filed Mar. 6, 2002 now U.S. Pat. No. 6,783,970, which is a divisional of application Ser. No. 09/445,472 now U.S. Pat. No. 6,358,726, filed Dec. 8, 1999, which is the national stage under 35 U.S.C. 371 of PCT/JP98/02465, filed Jun. 4, 1998.

TECHNICAL FIELD

The present invention relates to a hyperthermostable protease useful as an enzyme for industrial use, a gene encoding the same and a method of producing the enzyme by genetic engineering technique.

BACKGROUND ART

A protease is an enzyme that cleaves peptide bonds in proteins. A number of such enzymes have been found in animals, plants and microorganisms. The protease is used as a reagent for laboratory use and as a pharmaceutical, as well as in industrial fields, for example, as an additive for a detergent, for processing foods and for chemical synthesis utilizing a reverse reaction. Therefore, it can be said that the protease is an extremely important enzyme for industries. Since high physical and chemical stability is required for a protease used in industrial fields, a thermostable enzyme is preferably used among others. Since proteases produced by bacteria of genus *Bacillus* exhibit relatively high thermostability, they are mainly used as proteases for industrial use. However, in search of a more superior enzyme, attempts have been made to obtain an enzyme from a microorganism growing at high temperature, for example, a thermophilic bacterium of genus *Bacillus* or a hyperthermophile.

For example, a hyperthermophile *Pyrococcus furiosus* is known to produce a protease (Appl. Environ. Microbiol., 56:1992–1998 (1990); FEMS Microbiol. Letters, 71:17–20 (1990); J. Gen. Microbiol., 137:1193–1199 (1991)).

In addition, a hyperthermophile, *Pyrococcus* sp. strain KOD1, is reported to produce a thiol protease (a cysteine protease) (Appl. Environ. Microbiol., 60:4559–4566 (1994)). Hyperthermophiles of genus *Thermococcus*, genus *Staphylothermus* and genus *Thermobacteroides* are also known to produce proteases (Appl. Microbiol. Biotechnol., 34:715–719 (1991)).

The proteases from the hyperthermophiles as described above have high thermostability. Therefore, it is expected that they may be used in place of the thermostable proteases currently in use or in a field in which use of a protease has not been considered.

However, most of the microorganisms producing these enzymes grow only at high temperature. For example, *Pyrococcus furiosus* needs to be cultured at 90–100° C. Culturing at such high temperature is disadvantageous in view of energy cost. Furthermore, the productivities of the proteases from the hyperthermophiles are lower than the productivities of the conventional microbial proteases. Thus, the methods for industrially producing the proteases from the hyperthermophiles have problems.

By the way, production of an enzyme by genetic engineering technique by isolating the gene for the enzyme of interest and introducing it into a host microorganism that can readily be cultured is currently common in the art. However, the gene for the enzyme introduced into the host is not always expressed so efficiently as expected. It is believed that the main cause is that the GC content or the codon usage of the introduced gene is different from those of the genes of the host. Therefore, it is necessary to optimize the expression method for each gene to be introduced and/or each host in order to accomplish a suitable productivity of an enzyme for the intended use.

OBJECTS OF THE INVENTION

The objects of the present invention are to provide a protease from a hyperthermophile which is advantageous for industrial use, to isolate a gene encoding the protease from the hyperthermophile, and to provide a method of producing the hyperthermostable protease using the gene by genetic engineering technique in order to solve the problems as described above.

SUMMARY OF THE INVENTION

Among proteases produced by hyperthermophiles, some may be classified into the subtilisin-type of alkaline proteases based on the amino acid sequence homology. When a gene for such a protease is introduced into *Bacillus subtilis* which is generally used for production by genetic engineering technique, the productivity of this enzyme is much less than that of a protein inherently produced by *Bacillus subtilis*.

The present inventors have studied intensively and found that, by placing a gene encoding a signal peptide (signal sequence) derived from a subtilisin upstream a protease gene derived from a hyperthermophile to be expressed, and modifying the amino acid sequence around the cleavage site, the gene of interest is expressed in *Bacillus subtilis* with high efficiency. Furthermore, it has been found that the expression level of the enzyme can be increased by deleting a portion that is not essential for the enzymatic activity in the protease gene derived from the hyperthermophile of interest. Thus, the present invention has been completed.

The present invention is outlined as follows. The first invention of the present invention is a thermostable protease having an amino acid sequence represented by the SEQ ID NO:1 of the Sequence Listing, and a protease having an amino acid sequence in which one or several amino acid residues are deleted, substituted, inserted or added in the amino acid sequence represented by the SEQ ID NO:1 of the Sequence Listing and having a thermostable protease activity.

The second invention of the present invention is a gene encoding the thermostable protease of the first invention, and a thermostable protease gene that hybridizes with the gene.

The third invention of the present invention is a gene to be used for producing a thermostable protease derived from a hyperthermophile by genetic engineering technique, characterized in that the gene encodes an amino acid sequence represented by formula I:

SIG-Ala-Gly-Gly-Asn-PRO [I] (SEQ ID NO:30)

wherein SIG represents an amino acid sequence of a signal peptide derived from a subtilisin, PRO represents an amino acid sequence of a protein to be expressed. Preferably, SIG is the amino acid sequence represented by the SEQ ID NO:3 of the Sequence Listing. Preferably, PRO is an amino acid sequence of a hyperthermostable protease derived from a hyperthermophile, more preferably, an amino acid sequence of a protease derived from *Pyrococcus furiosus*.

The fourth invention of the present invention relates to a method of producing a protein by genetic engineering technique, characterized in that the method comprises culturing a bacterium of genus *Bacillus* into which the gene of the third invention is introduced, and collecting the protein of interest from the culture.

The fifth invention of the present invention is a plasmid used for producing a protein by genetic engineering technique, characterized in that the gene of the third invention is inserted into the plasmid.

A mutation such as deletion, substitution, insertion or addition of one to several amino acid residues in an amino acid sequence may be generated in a naturally occurring protein including the protein disclosed by the present invention. Such mutation may be generated due to a polymorphism or a mutation of the gene encoding the protein, or due to a modification of the protein in vivo or during purification after synthesis may occur. Nevertheless, it is known that such a mutated protein may exhibit physiological and biological activities equivalent with those of a protein without a mutation. This is applicable to a protein in which such a mutation is introduced into its amino sequence artificially, in which case it is possible to generate a wide variety of mutations. For example, it is known that a polypeptide in which a cysteine residue in the amino acid sequence of human interleukin-2 (IL-2) is substituted with a serine residue retains an interleukin-2 activity (Science, 224:1431 (1984)). Thus, a protease having an amino acid sequence in which one or several amino acid residues are deleted, substituted, inserted or added in the amino acid sequence disclosed by the present invention and having a protease activity equivalent with that of the protease of the present invention is within the scope of the present invention.

As used herein, "a gene which hybridizes (with a particular gene)" is a gene having a base sequence similar to that of the particular gene. It is likely that a gene having a base sequence similar to that of a particular gene encodes a protein having an amino acid sequence and a function similar to those of the protein encoded by the particular gene. Similarity of base sequences of genes can be examined by determining whether or not the genes or portions thereof form a hybrid (hybridize) each other under stringent conditions. By utilizing this procedure, a gene that encodes a protein having a similar function with that of the protein encoded by the particular gene can be obtained. That is, a gene having a similar base sequence with that of the gene of the present invention can be obtained by using the gene obtained by the present invention or a portion thereof as a probe to carry out hybridization according to a known method. Hybridization can be carried out according to the method, for example, as described in T. Maniatis et al. eds., Molecular Cloning: A Laboratory Manual 2nd ed., published by Cold Spring Harbor Laboratory, 1989. More specifically, hybridization can be carried out under the following conditions. Briefly, a membrane onto which DNAs are immobilized is incubated in 6×SSC (1×SSC represents 0.15 M NaCl, 0.015 M sodium citrate, pH 7.0) containing 0.5%. SDS, 0.1% bovine serum albumin (BSA), 0.1% polyvinylpyrrolidone, 0.1% Ficoll 400, 0.01% denatured salmon sperm DNA at 50° C. for 12–20 hours with a probe. After incubation, the membrane is washed until the signals for the immobilized DNAs can be distinguished from background, starting from washing in 2×SSC containing 0.5% SDS at 37° C. while decreasing the SSC concentration down to 0.1× and raising the temperature up to 50° C.

Alternatively, instead of hybridization, a gene amplification method (e.g., PCR method) which employs portions of the base sequence of the gene obtained by the present invention as primers can be utilized. Whether or not the gene thus obtained encodes a protein having the function of interest can be determined by expressing the gene utilizing a suitable host and a suitable expression system and examining the activity of the resulting protein.

BRIEF DESCRIPTION OF THE DRAWINGS

FIGS. 2–5 compares the amino acid sequences of Protease PFUL (SEQ ID NO:6), Protease TCES (SEQ ID NO:12) and a subtilisin (SEQ ID NO:31).

DETAILED DESCRIPTION OF THE INVENTION

Figure 1:
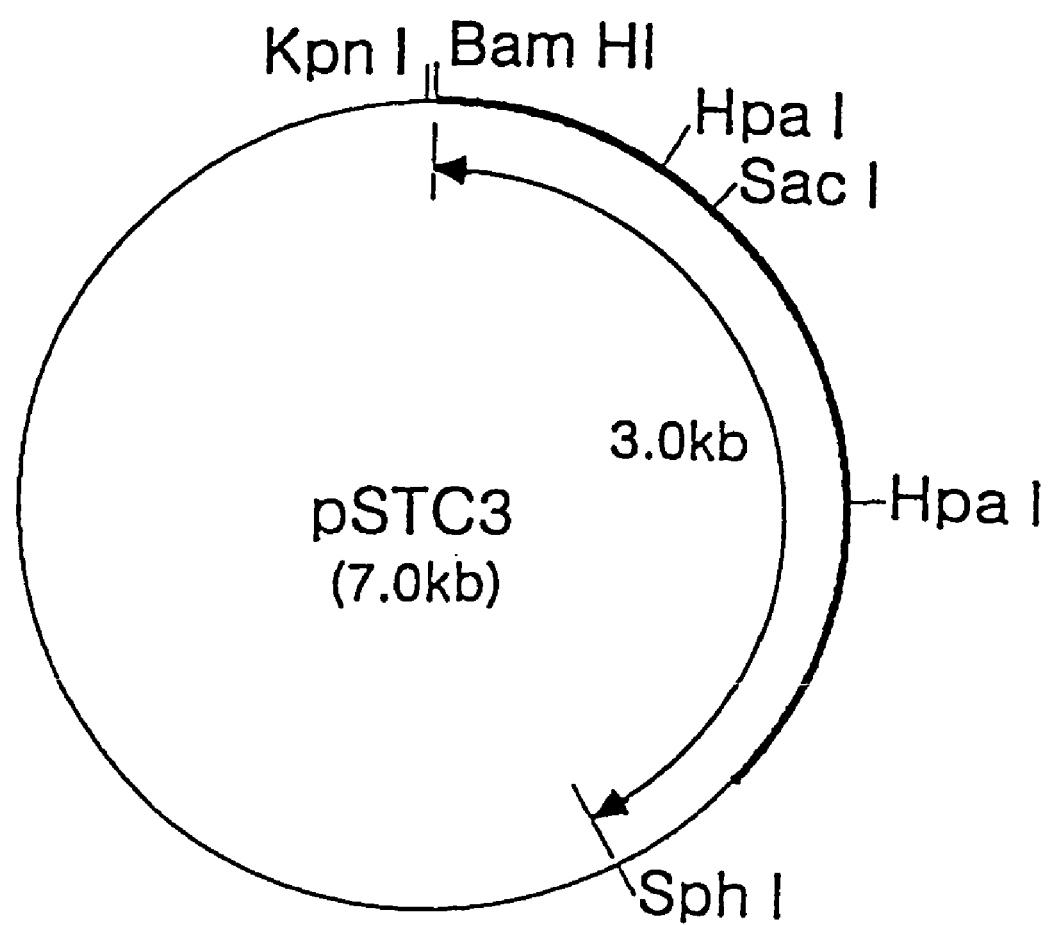
FIG. 1 is the restriction enzyme map of the plasmid pSTC3.

The hyperthermostable protease according to the present invention includes proteases from various hyperthermophiles. For example, WO 95/34645 describes proteases from *Pyrococcus furiosus* and *Thermococcus celer*.

A protease gene from *Pyrococcus furiosus* DSM3638 was isolated from a genomic DNA library of the strain based on the expression of a thermostable protease activity. A plasmid containing this gene is designated as the plasmid pTPR12. *Escherichia coli* JM109 transformed with this plasmid is designated and indicated as *Escherichia coli* JM109/pTPR12, and deposited on May 24, 1994 (the date of the original deposit) under Budapest Treaty at the National Institute of Bioscience and Human-Technology, Agency of Industrial Science and Technology, Ministry of International Trade and Industry, 1–3, Higashi 1-chome, Tsukuba-shi, Ibaraki-ken, Japan under accession number FERM BP-5103.

This protease is designated as Protease PFUL hereinafter. Protease PFUL is a protease having high thermostability and exhibits a protease activity even at 95° C.

The base sequence of the DNA fragment derived from *Pyrococcus furiosus* inserted into the plasmid pTPR12 has been determined. The base sequence of the portion of approximately 4.8 kb bordered by two DraI sites in the DNA fragment inserted into the plasmid pTPR12 is shown in the SEQ ID NO:5 of the Sequence Listing. Furthermore, the amino acid sequence of the gene product deduced from the base sequence is shown in the SEQ ID NO:6 of the Sequence Listing. In other words, the amino acid sequence as shown in the SEQ ID NO:6 of the Sequence Listing is the amino acid sequence of Protease PFUL. As shown in the sequence, Protease PFUL consists of 1398 amino acid residues and is a protease with a high molecular weight of over 150,000.

Comparison of the amino acid sequence of Protease PFUL as shown in SEQ ID NO:6 of the Sequence Listing with known amino acid sequences of proteases from microorganisms has revealed that the amino acid sequence of the first half portion of Protease PFUL is homologous to those of a series of alkaline serine proteases represented by a subtilisin (Protein Engineering, 4:719–737 (1991)), and that there is extremely high homology around the four amino acid residues which are believed to be important for the catalytic activity of the protease.

As described above, it has been found that a region common among proteases derived from mesophiles is conserved in the amino acid sequence of Protease PFUL produced by a hyperthermophile *Pyrococcus furiosus*. Thus, it is expected that a homologous protease produced by a hyperthermophile other than *Pyrococcus furiosus* also has this region.

For example, a gene for a hyperthermostable protease can be screened by performing PCR using a chromosomal DNA from various hyperthermophiles as a template and the oligonucleotides PRO-1F, PRO-2F, PRO-2R and PRO-4R in combination as primers. These oligonucleotides are synthesized based on the base sequence in the Protease PFUL gene which encodes a region exhibiting high homology with subtilisins or the like within the amino acid sequence of Protease PFUL. The base sequences of oligonucleotides PRO-1F, PRO-2F, PRO-2R and PRO-4R are shown in the SEQ ID NOS:7, 8, 9 and 10 of the Sequence Listing, respectively.

As a hyperthermophile from which the protease according to the present invention is derived, a bacterium belonging to genus *Pyrococcus*, genus *Thermococcus*, genus *Staphylothermus*, genus *Thermobacteroides* and the like can be used. As a bacterium belonging to genus *Thermococcus*, for example, *Thermococcus celer* DSM2476 can be used. This strain is available from Deutsche Sammlung von Mikroorganismen und Zellkulturen GmbH. When performing PCR using a chromosomal DNA from *Thermococcus celer* DSM2476 as a template and a combination of the oligonucleotides PRO-1F and PRO-2R or the oligonucleotide PRO-2F and Pro-4R as primers, specific DNA fragments are amplified, indicating the presence of a protease gene. Furthermore, by creating recombinant plasmids in which the DNA fragments are inserted into an appropriate plasmid vector and determining the base sequences of the inserted DNA fragments by dideoxy method, the amino acid sequences encoded by the fragments can be deduced. As a result, it proved that such DNA fragments encode an amino acid sequence that is homologous to the amino acid sequences of Protease PFUL and alkaline serine proteases from various microorganisms and that the PCR-amplified DNA fragments were amplified from a protease gene as a template.

Next, a gene for a hyperthermostable protease (for example, a gene for a hyperthermostable protease produced by *Thermococcus celer*) can be obtained by screening a gene library from a hyperthermophile using the PCR-amplified DNA fragment or the oligonucleotide as described above as a probe.

For example, a phage clone containing the gene of interest can be obtained by performing plaque hybridization against a library using the PCR-amplified DNA fragment as a probe. Such library is generated by ligating lambda GEM-11 vector (Promega) and DNA fragments resulting from partial digestion of the chromosomal DNA from *Thermococcus celer* DSM2476 with a restriction enzyme Sau3AI, then packaging them into lambda phage particles by in vitro packaging method.

It is found that a protease gene exists in a SacI fragment of approximately 1.9 kb by analyzing a DNA fragment contained in a phage clone thus obtained. Furthermore, it is found that this fragment lacks the 5' region of the protease gene by determining its base sequence. The 5' region can be obtained by PCR using a cassette and cassette primers (Takara Shuzo Gene Technology Product Guide, 1994–1995, pp.250–251). Thus, a DNA fragment which covers the 5' region of the hyperthermostable protease gene which is absent in the plasmid pTCS6 can be obtained. Furthermore, the base sequence of the entire hyperthermostable protease gene derived from *Thermococcus celer* can be determined from the base sequences of the two DNA fragments.

The base sequence of an open reading frame found in the determined base sequence is shown in the SEQ ID NO:11 of the Sequence Listing, and the amino acid sequence deduced from the base sequence is shown in the SEQ ID NO:12 of the Sequence Listing. The base sequence of the gene encoding the hyperthermostable protease from *Thermococcus celer* and the amino acid sequence of the protease were thus determined. This protease is designated as Protease TCES.

An expression vector in which the entire Protease TCES gene is reconstituted by combining the two DNA fragments can be constructed. However, when using *Escherichia coli* as a host, a transformant into which the expression plasmid of interest had been introduced was not obtained, probably because the generation of the product expressed from the gene in cells may be harmful or lethal to *Escherichia coli*. In such a case, for example, it is possible to use *Bacillus subtilis* as a host for extracellular secretion of the protease and to determine the activity.

As a *Bacillus subtilis* strain, *Bacillus subtilis* DB104 can be used, which is a known strain as described in Gene, 83:215–233 (1989). As a cloning vector, the plasmid pUB18-P43 can be used, which is a generous gift from Dr. Sui-Lam Wong, University of Calgary. The plasmid contains a kanamycin-resistance gene as a selectable marker.

A recombinant plasmid in which the Protease TCES gene is inserted downstream the P43 promoter in the plasmid vector pUB18-P43 is designated as the plasmid pSTC3. *Bacillus subtilis* DB104 transformed with this plasmid is designated and indicated as *Bacillus subtilis* DB104/pSTC3, and was deposited on Dec. 1, 1995 (the date of the original deposit) under Budapest Treaty at the National Institute of Bioscience and Human-Technology, Agency of Industrial Science and Technology, Ministry of International Trade and Industry, 1–3, Higashi 1-chome, Tsukuba-shi, Ibaraki-ken, Japan under accession number FERM BP-5635.

The restriction enzyme map of the plasmid pSTC3 is shown in FIG. 1. In FIG. 1, the bold line indicates the DNA fragment inserted into the plasmid vector pUB18-P43.

A thermostable protease activity is found in either of the culture supernatant and the cell extract of the culture of *Bacillus subtilis* DB104/pSTC3.

Main properties of a crude enzyme preparation of the protease obtained from the culture of the transformant are as follows.

(1) Action:

Degrades casein and gelatin to generate short chain polypeptides.

Hydrolyzes succinyl-L-leucyl-L-leucyl-L-valyl-L-tyrosine -4-methylcoumarin-7-amide (Suc-Leu-Leu-Val-Tyr-MCA) SEQ ID NO:32 to generate a fluorescent substance (7-amino-4-methylcoumarin).

Hydrolyzes succinyl-L-alanyl-L-alanyl-L-prolyl-L-phenylalanine -p-nitroanilide (Suc-Ala-Ala-Pro-Phe-p-NA) SEQ ID NO:33 to generate a yellow substance (p-nitroaniline).

(2) Optimal Temperature:

Exhibits an enzymatic activity at 37–95° C., with the optimal temperature being 70–80° C.

(3) Optimal pH:

Exhibits an enzymatic activity at pH 5.5–9, with the optimal pH being pH 7–8.

(4) Thermostability:

Retains 90% or more of its enzymatic activity after treatment at 80° C. for 3 hours.

When aligning the amino acid sequences of Protease PFUL, Protease TCES and a subtilisin (subtilisin BNP'; Nucl. Acids Res., 11:7911–7925 (1983)) such that homologous regions match each other as shown in FIGS. 2–5, it is found that, at the C-terminus and between the homologous regions of Protease PFUL, there are sequences which are not found in Protease TCES or the subtilisin. From these results, a protease having a molecular weight lower than that of Protease PFUL and similar to Protease TCES or subtilisins may exist in *Pyrococcus furiosus* in addition to Protease PFUL.

Thereupon, Southern hybridization against a chromosomal DNA prepared from *Pyrococcus furiosus* was carried out using a DNA Probe from the homologous region, and a signal other than that for the Protease PFUL gene was observed, indicating the existence of another protease gene.

This novel protease gene can be isolated by the following procedure.

For example, a DNA fragment containing a gene encoding the novel protease is obtained by digesting a chromosomal DNA from *Pyrococcus furiosus* with an appropriate restriction enzyme and performing Southern hybridization against the digested DNA as described above. The base sequence of the DNA fragment is determined to confirm that the base sequence encodes an amino acid sequence homologous to the above-mentioned protease. If the DNA fragment does not contain the entire gene of interest, the remaining portion is further obtained by inverse PCR method or the like.

For example, when a chromosomal DNA from *Pyrococcus furiosus* is digested with restriction enzymes SacI and SpeI (Takara Shuzo) and is used for Southern hybridization, a signal of approximately 0.6 kb in size is observed. DNA fragments of this size are recovered, inserted between the SpeI-SacI sites in the plasmid vector pBluescript SK(−) (Stratagene), and *Escherichia coli* JM 109 is transformed with the resulting recombinant plasmids. A clone into which the fragment of interest is incorporated can be obtained from the transformants by colony hybridization using the same probe as that used for the Southern hybridization as described above. Whether or not the plasmid harbored by the obtained clone has the sequence that encodes the protease can be confirmed by determining the base sequence of the DNA fragment inserted into the plasmid. The presence of the protease gene in the plasmid was thus confirmed. This plasmid is designated as the plasmid pSS3.

It is found that the amino acid sequence deduced from the base sequence of the DNA fragment inserted into the plasmid pSS3 has homology with sequences of subtilisins, Protease PFUL, Protease TCES and the like. The product of the protease gene distinct from the Protease PFUL gene, a portion of which was newly obtained from *Pyrococcus furiosus* as described above, is designated as Protease PFUS. The regions which encode the N-terminal and C-terminal regions of the protease can be obtained by inverse PCR method.

Primers used for inverse PCR can be prepared based on the base sequence of the DNA fragment inserted into the plasmid pSS3. A chromosomal DNA from *Pyrococcus furiosus* is digested with an appropriate restriction enzyme, and the resulting DNA fragments are then subjected to an intramolecular ligation reaction. By performing PCR using the reaction mixture as a template and the above-mentioned primers, DNA fragments corresponding to the regions flanking the fragment for the protease gene contained in the plasmid pSS3 can be obtained. The amino acid sequence of the enzyme protein encoded by these regions can be deduced by analyzing the base sequences of the DNA fragments thus obtained. Furthermore, primers capable of amplifying the entire Protease PFUS gene using a chromosomal DNA from *Pyrococcus furiosus* as a template can be prepared. The primers NPF-4 and NPR-4 can be designed. The primer NPF-4 has the base sequence immediately upstream the initiation codon of the Protease PFUS gene and can introduce a BamHI site 5' to the sequence. The primer NPR-4 has a sequence complementary to the 3' portion of the Protease PFUS gene and can introduce a SphI site 5' to the sequence.

The base sequences of the primers NPF-4 and NPR-4 are shown in the SEQ ID NOS:13 and 14 of the Sequence Listing. These two primers can be used to amplify the entire Protease PFUS gene using a chromosomal DNA from *Pyrococcus furiosus* as a template.

Figure 6:
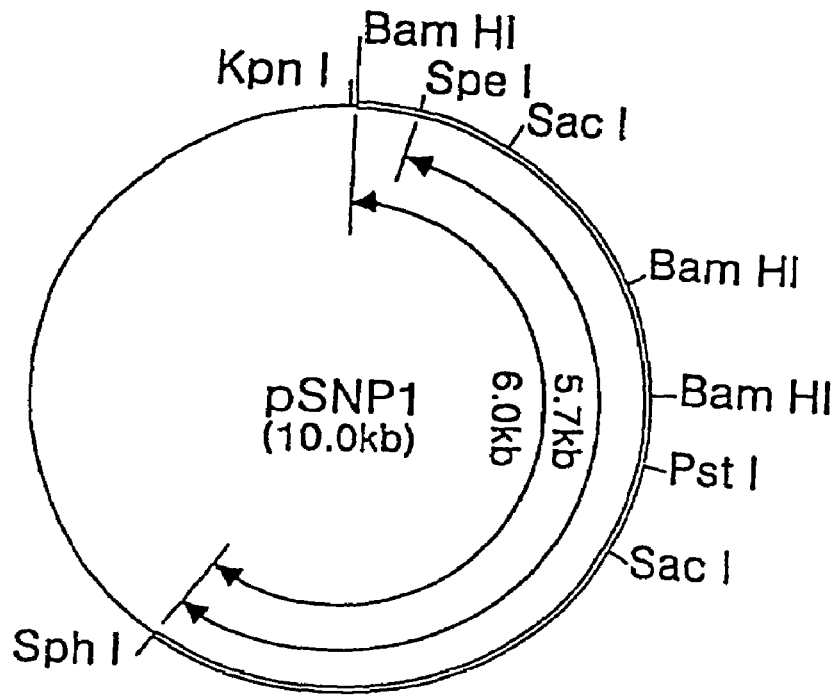
FIG. 6 is the restriction enzyme map of the plasmid pSNP1.

Like Protease TCES, Protease PFUS can be expressed in *Bacillus subtilis* as a host. A plasmid for expressing Protease PFUS can be constructed based on the expression plasmid for Protease TCES, pSTC3. Specifically, a plasmid for expressing Protease PFUS can be constructed by replacing the Protease TCES gene in the plasmid pSTC3 with the DNA fragment containing the entire Protease PFUS gene amplified by PCR with the primers as described above. The expression plasmid thus constructed is designated as the plasmid pSNP1. *Bacillus subtilis* DB104 transformed with this plasmid is designated and indicated as *Bacillus subtilis* DB104/pSNP1, and was deposited on Dec. 1, 1995 (the date of the original deposit) under Budapest Treaty at the National Institute of Bioscience and Human-Technology, Agency of Industrial Science and Technology, Ministry of International Trade and Industry, 1–3, Higashi 1-chome, Tsukuba-shi, Ibaraki-ken, Japan under accession number FERM BP-5634. The restriction enzyme map of the plasmid pSNP1 is shown in FIG. 6.

The base sequence corresponding to an open reading frame in the gene encoding Protease PFUS and the amino acid sequence of Protease PFUS deduced from the base sequence are shown in the SEQ ID NOS: 15 and 16 of the Sequence Listing, respectively.

A thermostable protease activity is found in either of the culture supernatant and the cell extract from the culture of *Bacillus subtilis* DB104/pSNP1. That is, a portion of the expressed Protease PFUS is secreted into the culture supernatant.

Main properties of the protease obtained from the culture of the transformant are as follows.

(1) Action:

Degrades casein and gelatin to generate short chain polypeptides.

Hydrolyzes succinyl-L-leucyl-L-leucyl-L-valyl-L-tyrosine-4-methylcoumarin-7-amide (Leu-Leu-Val-Tyr-MCA) SEQ ID NO: 32 to generate a fluorescent substance (7-amino-4-methylcoumarin).

Hydrolyzes succinyl-L-alanyl-L-alanyl-L-prolyl-L-phenylalanine-p-nitroanilide (Suc-Ala-Ala-Pro-Phe-p-NA) SEQ ID NO:33 to generate a yellow substance (p-nitroaniline)

(2) Optimal Temperature:

Exhibits an enzymatic activity at 40–110° C., with the optimal temperature being 80–95° C.

(3) Optimal pH:

Exhibits an enzymatic activity at pH 5–10, with the optimal pH being pH 6–8.

(4) Thermostability:

Retains 90% or more of its enzymatic activity after treatment at 95° C. for 8 hours.

(5) pH Stability

Retains 95% or more of its activity after treatment at pH 5–11 at 95° C. for 60 minutes.

(6) Molecular Weight

Exhibits a molecular weight of approximately 45 kDa on SDS-PAGE.

Protease genes homologous to the Protease TCES gene and the Protease PFUS gene can be obtained from hyperthermophiles other than *Pyrococcus furiosus* and *Thermococcus celer* using a method similar to that used to obtain the Protease TCES gene and the Protease PFUS gene.

A DNA fragment of approximately 1 kb which encodes a sequence from the residue at position 323 to the residue at position 650 of the amino acid sequence of Protease PFUL as shown in the SEQ ID NO:6 of the Sequence Listing can be prepared and used as a probe for genomic Southern hybridization against chromosomal DNAs from *Staphylothermus marinus* DSM3639 and *Thermobacteroides proteoliticus* DSM 5265. As a result, signals are observed at the position of approximately 4.8 kb for the chromosomal DNA from *Staphylothermus marinus* digested with PstI (Takara Shuzo) and at the position of approximately 3.5 kb for the chromosomal DNA from *Thermobacteroides proteoliticus* digested with XbaI.

From these results, it proved that there are sequences homologous to those of the genes for Protease PFUL, Protease PFUS and Protease TCES and the like on the chromosomal DNAs from *Staphylothermus marinus* and *Thermobacteroides proteoliticus*. The genes encoding the hyperthermostable proteases in *Staphylothermus marinus* and *Thermobacteroides proteoliticus* can be isolated and identified from the DNA fragments thus detected by using a method similar to that used to isolate and identify the genes encoding Protease TCES and Protease PFUS.

In general, it is believed that use of a promoter that acts effectively in a host rather than a promoter that is inherently associated with the gene encoding the protein of interest would be advantageous in order to prepare a protein in a large quantity by genetic engineering technique. Although the P43 promoter used to construct the expression systems for Protease TCES and Protease PFUS is a promoter derived from *Bacillus subtilis*, it was not sufficiently effective to express the two proteases.

Thereupon, a gene that is expressed at high level in *Bacillus subtilis*, particularly a gene for a secreted protein, may be utilized in order to increase the expression level. Genes for α-amylase or various extracellular proteases can be used. For example, it is expected that use of a promoter and a signal peptide-encoding region of a subtilisin gene may increase the expression level of Protease PFUS.

Specifically, Protease PFUS can be expressed as a fused protein under control of the promoter of the subtilisin gene by placing the entire Protease PFUS gene downstream the region encoding the signal peptide of, the subtilisin gene including the promoter region such that the translational frames of the two genes match each other.

For example, the gene encoding subtilisin E can be used as the subtilisin gene used in the present invention. The promoter and the signal peptide-encoding region of the subtilisin E gene inserted in the plasmid pKWZ as described in J. Bacteriol., 171:2657–2665. (1989) can be used. The base sequence of the 5' upstream region including the promoter sequence is described in the reference (supra) and the base sequence of the region encoding the subtilisin is described in J. Bacteriol., 158:411–418 (1984).

Based on these sequences, the primer SUB4 for introducing an EcoRI site upstream the promoter sequence of the gene and the primer BmR1 for introducing a BamHI site downstream the region encoding the signal peptide of subtilisin E are synthesized. The base sequences of the primers SUB4 and BmR1 are shown in the SEQ ID NOS:17 and 18 of the Sequence Listing, respectively. The primers SUB4 and BmR1 can be used to amplify a DNA fragment of approximately 0.3 kb containing the promoter and the signal peptide-encoding region of the subtilisin E gene by PCR using the plasmid pKWZ as a template.

The Protease PFUS gene to be placed downstream the DNA fragment can be obtained from a chromosomal DNA from *Pyrococcus furiosus* by PCR method. The primer NPF-4 can be used as a primer that hybridizes with the 5' region of,the gene. The primer NPM-1, which is designed based on the base sequence downstream from the termination codon of the gene and has a SphI site, can be used as a primer which hybridizes with the 3' region of the gene. The sequence of the primer NPM-1 is shown in the SEQ ID NO:19 of the Sequence Listing.

One BamHI site present in the gene would become a problem for a procedure in which a BamHI site is utilized for joining the Protease PFUS gene to the 0.3 kb DNA fragment. The primers mutRR and mutFR for eliminating the BamHI site by PCR-mutagenesis method can be prepared based on the base sequence of the Protease PFUS gene as shown in the SEQ ID NO:15 of the Sequence Listing. The base sequences of the primers mutRR and mutFR are shown in the SEQ ID NOS:20 and 21 of the Sequence Listing, respectively. When these primers are used to eliminate the BamHI site, the amino acid residue encoded by this site, i.e., glycine at position 560 in the amino acid sequence of Protease PFUS as shown in the SEQ ID NO:16 of the Sequence Listing, is substituted by valine due to the base substitution introduced into the site.

The Protease PFUS gene to be joined to the promoter and the signal peptide-encoding region of the subtilisin E gene can be obtained by using these primers. Specifically, two PCRs are performed using a chromosomal DNA from *Pyrococcus furiosus* as a template and the pair of the primers mutRR and NPF-4 or the pair of the primers mutFR and NPM-1. In addition, a second round of PCR is performed using a heteroduplex formed by mixing the respective PCR-amplified DNA fragments as a template and the primers NPF-4 and NPM-1. Thus, the entire Protease PFUS gene of approximately 2.4 kb which does not contain an internal BamHI site can be amplified.

Figure 7:
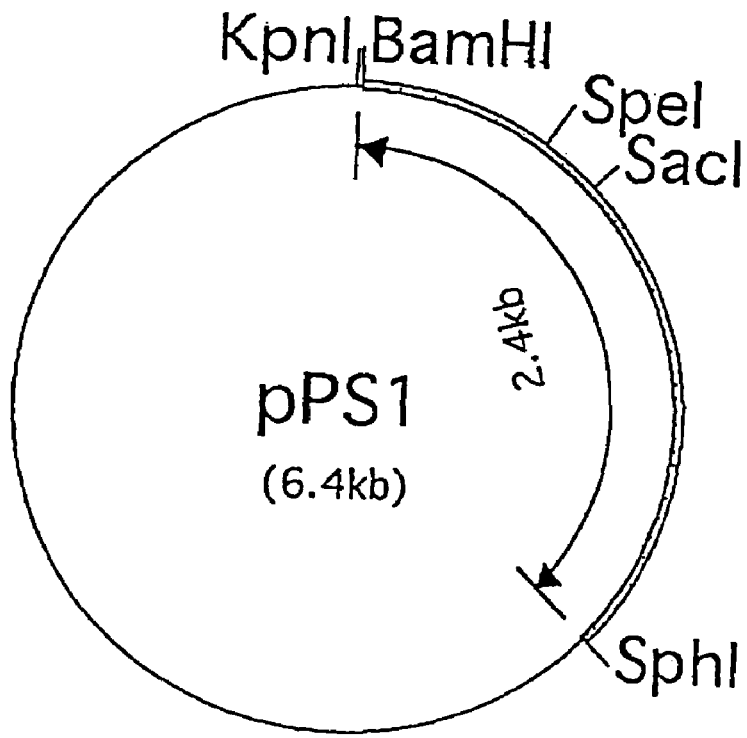
FIG. 7 is the restriction enzyme map of the plasmid pPS1.

A DNA fragment of approximately 2.4 kb obtained by digesting the PCR-amplified DNA fragment with BamHI and SphI is isolated and used to replace a BamHI-SphI fragment in the plasmid pSNP1 which contains the Protease PFUS gene. An expression vector thus constructed is designated as the plasmid pPS1. *Bacillus subtilis* DB104 transformed with this plasmid is designated as *Bacillus subtilis* DB104/pPS1. A similar protease activity is found in either of the culture supernatant and the cell extract of the culture of this transformant as observed for the transformant harboring the plasmid pSNP1, demonstrating that the amino acid substitution does not influence the enzymatic activity. The restriction enzyme map of the plasmid pPS1 is shown in FIG. 7.

Figure 8:
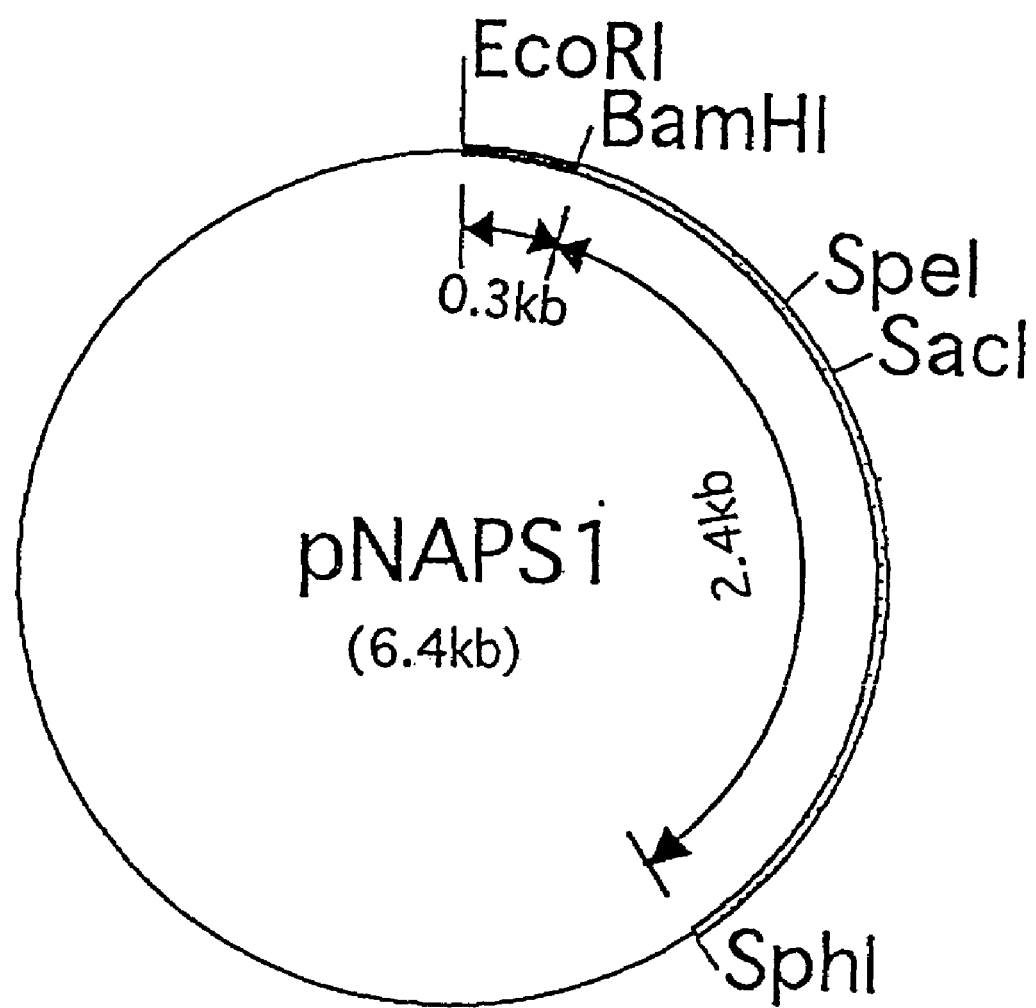
FIG. 8 is the restriction enzyme map of the plasmid pNAPS1.

The DNA fragment of approximately 0.3 kb containing the promoter and the signal peptide-encoding region of the subtilisin E gene is digested with EcoRI and BamHI and is used to replace the EcoRI-BamHI fragment containing the P43 promoter and a ribosome binding site in the plasmid pPS1. An expression plasmid thus constructed is designated as pNAPS1. Bacillus subtilis DB104 transformed with this plasmid is designated as Bacillus subtilis DB104/pNAPS1. A thermostable protease activity is found in either of the culture supernatant and the cell extract of the culture of the transformant, with the expression level being increased as compared with that of Bacillus subtilis DB104/pSNP1. The restriction enzyme map of the plasmid pNAPS1 is shown in FIG. 8.

The protease expressed from the transformant exhibits enzymological properties equivalent to those of the protease expressed by Bacillus subtilis DB104/pSNP1 as described above. The protease expressed by the transformant was purified. The analysis of the N-terminal amino acid sequence of the purified protease provided the amino acid sequence as shown in the SEQ ID NO:22 of the Sequence Listing. This sequence is identical with the sequence from position 133 to position 144 of the amino acid sequence of Protease PEUS as shown in the SEQ ID NO:16 of the Sequence Listing, indicating that the mature Protease PFUS is an enzyme consisting of a polypeptide starting from this portion. The amino acid sequence of the mature Protease PFUS assumed from these results is shown in the SEQ ID NO:4 of the Sequence Listing.

Although the amount of the protease produced by Bacillus subtilis DB104/pNAPS1 is increased as compared with the amount of the protease produced by Bacillus subtilis DB104/pSNP1 (FERM BP-5634), higher productivity is desired. It is expected that the expression level of the protease is increased by modifying the junction of the fused peptide encoded by pNAPS1 between the signal peptide of the subtilisin and Protease PFUS to make the removal of the signal peptide more efficient. In the plasmid pNAPS1, a peptide consisting of three amino acid residues Ala-Gly-Ser is inserted between the C-terminal amino acid residue of the signal peptide of subtilisin E as shown in the SEQ ID NO:3 of the Sequence Listing (Ala) and the N-terminal amino acid residue of Protease PFUS (Met). A transformant with increased expression level of the protease can be obtained by introducing a mutation into the DNA encoding this peptide in the plasmid pNAPS1 and examining the protease productivity of the transformant into which the mutant plasmid is introduced.

First, a mutant plasmid is prepared in which the portion encoding Ser in the three amino acid peptide in the gene encoding the fused protein, subtilisin E-Protease PFUS, in the plasmid pNAPS1 is modified such that the base sequence of the portion encodes random two amino acid residues. Such a mutant plasmid can be created by means of PCR. For example, the primers SPOF0 and SPOR0 having sequences in which the codon encoding Ser (TCC) is substituted by random six bases (the base sequences of the primers SPOF0 and SPOR0 are shown in the SEQ ID NOS:24 and 25 of the Sequence Listing, respectively) and the primers SUB3 and NPR-10 which are prepared based on the base sequence around this region (the base sequences of the primers SUB3 and NPR-10 are shown in the SEQ ID NOS:26 and 27 of the Sequence Listing, respectively) can be used to perform PCR to obtain a DNA fragment into which the intended mutation at the portion corresponding to the codon encoding Ser (TCC) is introduced. A mutant plasmid containing the protease gene with the introduced mutation can be obtained by replacing the resulting fragment for the corresponding region in the plasmid pNAPS1.

A transformant with increased expression level can be then obtained by introducing the mutant plasmids thus obtained into an appropriate host, for example, Bacillus subtilis DB104, and determining the level of the protease expressed by the transformants. The expression level of the protease can be confirmed by determining the activity in the independent culture of the isolated transformant. Alternatively, a transformant with increased expression level can be readily selected by using an agar plate containing a substrate.

Specifically, the transformants into which the mutant plasmids are introduced are grown on agar plates containing skim milk. Thereafter, the plates are incubated at temperature at which Protease PFUS exhibits its activity, for example, at 70° C. Skim milk around a colony of a transformant expressing a protease is degraded to become clear. The expression level of the protease can be estimated from the size of the clear zone.

One of the transformants thus obtained which express high level of protease activity as compared with Bacillus subtilis DB104/pNAPS1 is designated as Bacillus subtilis DB104/pSPO124. The plasmid contained in this transformant was prepared (this plasmid is designated as pSPO124). Analysis of the base sequence of the plasmid revealed that the portion encoding Ser was changed into a base sequence GGGAAT, that is, that a protein in which Ser was changed into Gly-Asn was encoded by the plasmid.

Thus, it proved that the expression level of the protein of interest can be increased in a bacterium of genus Bacillus as a host by placing a peptide consisting of four amino acid residues Ala-Gly-Gly-Asn (SEQ ID NO:30) downstream the signal peptide of a subtilisin, fusing it to the N-terminus of the protein of interest and expressing the fused protein. In addition to subtilisin E (from Bacillus subtilis) which is used in the present invention, subtilisin BPN[1] from Bacillus amyloliquefaciens (Nucl. Acids Res., 11:7911–7925 (1983)), subtilisin Carlsberg from Bacillus licheniformis (Nucl. Acids Res., 13:8913–8926 (1985)) and the like are known as subtilisins produced by bacteria of genus Bacillus. The signal peptides from them can be preferably used for the present invention although their amino acid sequences slightly vary each other. Various promoters which function in a bacterium of genus Bacillus can be used in place of the promoter from the subtilisin E gene which is used in the present invention for controlling expression.

There is no limitation regarding the protein to be expressed. It is possible to express a protein at high level by genetic engineering technique by applying the present invention as long as the gene for the protein is available. It is evident that the present invention can be utilized to express a protein derived from an organism other than the host from the fact that a protein derived from Pyrococcus furiosus, which is taxonomically different from bacteria of genus Bacillus, is expressed at high level. The present invention is preferably used to produce Protease PFUL, Protease TCES as well as proteases from Staphylothermus marinus and Thermobacteroides proteoliticus that are structurally similar to Protease PFUS by genetic engineering technique.

Based on the homology with subtilisins, it is considered that Protease PFUS is expressed as a precursor protein having a signal peptide and a propeptide and then subjected to processing to generate a mature enzyme. Furthermore, based on the results of the N-terminal amino acid sequence analysis of the mature Protease PFUS enzyme, it may be assumed that the mature enzyme is an enzyme consisting of the amino acid sequence as shown in the SEQ ID NO:4 of the Sequence Listing. However, the molecular weight of the purified mature Protease PFUS is approximately 45 kDa which is smaller than that calculated from the amino acid sequence, suggesting that Protease PFUS expressed as a precursor is converted to a mature protease after being subjected to processing of its C-terminal peptide as well.

If the C-terminal peptide removed by the processing is not essential to the enzymatic activity or the folding of the enzyme protein into proper structure, it is expected that the expression level of Protease PFUS can be also increased by deleting the region encoding this portion from the gene and expressing the protease.

The molecular weight of the mature Protease PFUS obtained from *Bacillus subtilis* DB104/pNAPS1 can be precisely measured, for example, by using a mass spectrometer. It is found from the measured molecular weight and the N-terminal amino acid sequence of the mature Protease PFUS determined as described above that the protease is a polypeptide corresponding to Ala at position 133 to Thr at position 552 of the amino acid sequence as shown in the SEQ ID NO:16 of the Sequence Listing. Furthermore, a plasmid which expresses Protease PFUS lacking a polypeptide nonessential for its enzymatic activity can be constructed by introducing a termination codon in the vicinity of the portion encoding Thr at position 552 in the Protease PFUS gene contained in the plasmid pNAPS1. Specifically, a DNA fragment having a base sequence into which the intended termination codon is introduced can be obtained by PCR using the primer NPR544 which can introduce a termination codon (TGA) on the C-terminal side of the 544th amino acid residue encoding codon from the initiation codon in the Protease PFUS gene in the plasmid pNAPS1 (Ser) (the base sequence of the primer NPR544 is shown in the SEQ ID NO:28 of the Sequence Listing) and the primer NPFE81 which has the base sequence of the region upstream from the NspV site in the gene (the base sequence of the primer NPFE81 is shown in the SEQ ID NO:29 of the Sequence Listing). A mutant plasmid containing the protease gene into which the mutation of interest is introduced can be then obtained by replacing the fragment for the corresponding region in the plasmid pNAPS1. This plasmid is designated as the plasmid pNAPSΔC. *Bacillus subtilis* DB104 transformed with this plasmid is designated as *Bacillus subtilis* DB104/pNAPSΔC.

This transformant expresses a protease activity having properties equivalent to those of Protease PFUS, with the expression level being higher than that of *Bacillus subtilis* DB104/pNAPS1.

Thus, it was found that the Protease PFUS gene contained in the plasmid pNAPSΔC has a sufficient region to express the activity of the enzyme. The base sequence of the region encoding Protease PFUS present in the plasmid is shown in the SEQ ID NO:2 of the Sequence Listing. The amino acid sequence encoded by the base sequence is shown in the SEQ ID NO:1 of the Sequence Listing.

Furthermore, Protease PFUS lacking its C-terminal peptide can be expressed by introducing a mutation similar to that in the plasmid pNAPSΔC into the Protease PFUS gene in the plasmid pSPO124.

Specifically, the plasmid of interest can be constructed by mixing and ligating a DNA fragment of approximately 13 kb obtained by digesting the plasmid pNAPSΔC with NspV and SphI with the plasmid pSPO124 that has been digested with NspV and SphI. This plasmid is designated as the plasmid pSO124ΔC. *Bacillus subtilis* DB104 transformed with this plasmid is designated and indicated as *Bacillus subtilis* DB104/pSO124ΔC, and deposited on May 16, 1997 (the date of the original deposit) under Budapest Treaty at the National Institute of Bioscience and Human-Technology, Agency of Industrial Science and Technology, Ministry of International Trade and Industry, 1–3, Higashi 1-chome, Tsukuba-shi, Ibaraki-ken, Japan under accession number FERM BP-6294. The expression level of protease of this transformant is increased as compared with that of *Bacillus subtilis* DB104/pNAPS1.

The enzymological properties as well as the physical and chemical properties of the proteases produced by the transformants, *Bacillus subtilis* DB104/pNAPSΔC and *Bacillus subtilis* DB104/pSPO124ΔC appear to be identical with those of the protease produced by *Bacillus subtilis* DB104/pSNP1. The main properties of the proteases obtained from the cultures of the two transformants are as follows:

(1) Action:

Degrades casein and gelatin to generate short chain polypeptides.

Hydrolyzes succinyl-L-leucyl-L-leucyl-L-valyl-L-tyrosine -4-methylcoumarin-7-amide (Suc-Leu-Leu-Val-Tyr-MCA) SEQ ID NO:32 to generate a fluorescent substance (7-amino-4-methylcoumarin).

Hydrolyzes succinyl-L-alanyl-L-alanyl-L-prolyl-L-phenylalanine -p-nitroanilide (Suc-Ala-Ala-Pro-Phe-p-NA) SEQ ID NO:33 to generate a yellow substance (p-nitroaniline).

(2) Optimal Temperature:

Exhibits an enzymatic activity at 40–110° C., with the optimal temperature being 80–95° C.

(3) Optimal pH:

Exhibits an enzymatic activity at pH 5–10, with the optimal pH being pH 6–8.

(4) Thermostability:

Retains 90% or more of its enzymatic activity after treatment at 95° C. for 8 hours.

(5) pH Stability

Retains 95% or more of its activity after treatment at pH 5–11 at 95° C. for 60 minutes.

(6) Molecular Weight

Exhibits a molecular weight of approximately 45 kDa on SDS-PAGE.

Thus, proteases having high thermostability and genes therefor are provided. Also, a novel system for expressing a protein, which enables the expression of the protease in large quantity is disclosed by the present invention. The expression system is useful in production of the protease of the present invention as well as various proteins by genetic engineering technique.

The following Examples illustrate the present invention in more detail, but are not to be construed to limit the scope thereof.

EXAMPLE 1

(1) Preparation of a Chromosomal DNA from *Pyrococcus furiosus*

*Pyrococcus furiosus* DSM3638 was cultured as follows.

A medium containing 1% Tryptone, 0.5% yeast extract, 1% soluble starch, 3.5% Jamarine S Solid (Jamarine Laboratory), 0.5% Jamarine S Liquid (Jamarine Laboratory), 0.003% $MgSO_4$, 0.001% NaCl, 0.0001% $FeSO_4.7H_2O$, 0.0001% $CoSO_4$, 0.0001% $CaCl_2.7H_2O$, 0.0001% $ZnSO_4$, 0.1 ppm $CUSO_4.5H_2O$, 0.1 ppm $H_3BO_3$, 0.1 ppm $KAl(SO_4)_2$, 0.1 ppm $Na_2MoO_4.2H_2O$, 0.25 ppm $NiCl_2.H_2O$ was placed in a 2 L medium bottle, sterilized at 120° C. for 20 minutes, bubbled with nitrogen gas to remove dissolved oxygen, then the strain was inoculated into the medium and cultured at 95° C. for 16 hours without shaking. After cultivation, cells were collected by centrifugation.

The resulting cells were then suspended in 4 mL of 50 mM Tris-HCl (pH 8.0) containing 25% sucrose. 2 mL of 0.2 M EDTA and 0.8 mL of lysozyme (5 mg/mL) were added to the suspension. The mixture was incubated at 20° C. for 1 hour. 24 mL of SET solution (150 mM NaCl, 1 mM EDTA, 20 mM Tris-HCl, pH 8.0), 4 mL of 5% SDS and 400 μL of proteinase K (10 mg/mL) were then added to the mixture. Incubation was further carried out at 37° C. for 1 hour. The reaction was terminated by extracting the mixture with phenol-chloroform. Then, ethanol precipitation was carried out to obtain approximately 3.2 mg of chromosomal DNA.

EXAMPLE 2

(1) Synthesis of Primers for Constructing the Plasmid pNSP1

In order to synthesize primers used to amplify the entire Protease PFUS gene, the plasmid pSNP1 that contains the entire gene was isolated from *Bacillus subtilis* DB104/pSNP1 (FERM BP-5634) and the base sequence of the required region was determined. Based on the base sequence, the primer NPF-4 for introducing a BamHI site immediately upstream the initiation codon of the Protease PFUS gene and the primer NPM-1 which hybridizes with the 3' region of the gene and contains a recognition site for SphI were synthesized. The base sequences of the primers NPF-4 and NPM-1 are shown in the SEQ ID NOS:13 and 19 of the Sequence Listing, respectively.

The primers mutRR and mutFR for removing the BamHI site present approximately 1.7 kb downstream from the initiation codon in the Protease PLUS gene were also synthesized. The base sequences of the primers mutRR and mutFR are shown in the SEQ ID NOS:20 and 21 of the Sequence Listing, respectively.

(2) Preparation of the Plasmid pPS1

Two sets of LA-PCR reaction mixtures each of which containing a chromosomal DNA from *Pyrococcus furiosus* as a template and a combination of the primers NPF-4 and mutRR or a combination of the primers mutFR and NPM-1 were prepared and subjected to 30 cycles of reactions of 94° C. for 30 seconds—55° C. for 1 minute—68° C. for 3 minutes. LA PCR Kit Ver. 2 (Takara Shuzo) was used to prepare the LA-PCR reaction mixtures. Aliquots of the reaction mixtures were subjected to agarose gel electrophoresis, and amplification of a DNA fragment of approximately 1.8 kb with the primers NPF-4 and mutRR and a DNA fragment of approximately 0.6 kb with the primers mutFR and NPM-1 were observed, respectively.

The primers were removed from the two PCR reaction mixtures using SUPREC-02 (Takara Shuzo) to prepare amplified DNA fragments. An LA-PCR reaction mixture which contained these two amplified DNA fragments and did not contain the primers or LA Taq was prepared, heat-denatured at 94° C. for 10 minutes, cooled to 30° C. within 30 minutes, then incubated at 30° C. for 15 minutes to form a heteroduplex. Subsequently, LA Taq (Takara Shuzo) was added to the reaction mixture to react at 72° C. for 30 minutes. The primers NPF-4 and NPM-1 were then added to the reaction mixture, which was then subjected to 25 cycles of reactions of 94° C. for 30 seconds—55° C. for 1 minute—68° C. for 3 minutes. Amplification of a DNA fragment of approximately 2.4 kb was observed in the reaction mixture.

The DNA fragment of approximately 2.4 kb was digested with BamHI and SphI (both from Takara Shuzo). The fragment was mixed and ligated with the plasmid pSNP1 which had been digested with BamHI and SphI to remove the entire Protease PFUS gene, then introduced into *Bacillus subtilis* DB104. Plasmids were prepared from resulting kanamycin-resistant transformants, and a plasmid into which only one molecule of the fragment of approximately 2.4 kb was inserted was selected and designated as the plasmid pPS1. *Bacillus subtilis* DB104 transformed with this plasmid pPS1 was designated as *Bacillus subtilis* DB104/pPS1.

The restriction enzyme map of the plasmid pPS1 is shown in FIG. 7.

(3) Amplification of a DNA Fragment for the Promoter-Signal Peptide-Encoding Region of the Subtilisin E Gene Primers for obtaining the promoter-signal peptide-encoding region of the subtilisin E gene were synthesized. First, the primer SUB4 was synthesized based on the base sequence of the promoter region of the subtilisin E gene as described in J. Bacteriol., 171:2657–2665 (1989), which hybridizes with the sequence upstream this region and contains an EcoRI site (the base sequence of the primer SUB4 is shown in the SEQ ID NO:17 of the Sequence Listing). The primer BmR1 which is capable of introducing a BamHI site immediately downstream the signal peptide-encoding region was synthesized based on the base sequence of the subtilisin E gene as described in J. Bacteriol., 158: 411–418 (1984) (the base sequence of the primer BmR1 is shown in the SEQ ID NO:18 of the Sequence Listing).

A PCR reaction mixture containing the plasmid pKWZ, which contains the subtilisin E gene as described in J. Bacteriol., 171:2657–2665, as a template and the primers SUB4 and BmR1 was prepared and subjected to 30 cycles of reactions of 94° C. for 30 seconds—55° C. for 1 munute—68° C. for 2 minutes. An aliquot of the reaction mixture was subjected to agarose gel electrophoresis, and amplification of a DNA fragment of approximately 0.3 kb was observed.

(4) Construction of the Protease Expression Plasmid pNAPS1

The DNA fragment of approximately 0.3 kb as described above was digested with EcoRI (Takara Shuzo) and BamHI, mixed and ligeted with the plasmid pPS1 described in Example 3 which had been digested with EcoRI and BamHI, then introduced into *Bacillus subtilis* DB104. Plasmids were prepared from resulting kanamycin-resistant transformants, and a plasmid into which only one molecule of the fragment of approximately 0.3 kb was inserted was selected and designated as the plasmid pNAPS1. *Bacillus subtilis* DB104 transformed with the plasmid pNAPS1 was designated as *Bacillus subtilis* DB104/pNAPS1.

The restriction enzyme map of the plasmid pNAPS1 is shown in FIG. 8.

(5) Construction of the Plasmid pSNP2

The primer SUB17R for introducing a BamHI site upstream the signal peptide-encoding region of the subtilisin E gene in the above-mentioned plasmid pNAPS1 was synthesized (the base sequence of the primer SUB17R is shown in the SEQ ID NO:23 of the Sequence Listing). A PCR reaction mixture containing the plasmid pNAPS1 as a template and the primers SUB17R and SUB4 was prepared and subjected to 25 cycles of reactions of 94° C. for 30 seconds—55° C. for 1 munute—72° C. for 1 minute. The amplified DNA fragment of approximately 0.21 kb was digested with EcoRI and BamHI to obtain a DNA fragment of approximately 0.2 kb that contains the promoter and the SD sequence of the subtilisin E gene. This fragment was mixed and ligated with the plasmid pNAPS1 that had been digested with EcoRI and BamHI. The reaction mixture was used to transform *Bacillus subtilis* DB104. Plasmids were prepared from resulting kanamycin-resistant transformants, and a plasmid into which the DNA fragment of approximately 0.2 kb was inserted was selected and designated as the plasmid pSNP2.

(6) Generation of a Mutant Plasmid which Expresses a Protease at High Level

The primers SPOF0 and SPOR0 for substituting the sequence encoding the amino acid residue Ser (base sequence: TCC) at the junction between the signal peptide-encoding region of the subtilisin E gene in the plasmid pNAPS1 and the initiation codon of the Protease PFUS gene with a sequence for two random amino acid residues were synthesized (the base sequences of the primers SPOF0 and SPOR0 are shown in the SEQ ID NOS:24 and 25 of the Sequence Listing, respectively). The primer SUB3 for introducing a BamHI site immediately upstream the signal peptide-encoding region in the subtilisin E gene in the plasmid pNAPS1 and the primer NPR-10 which contains a SpeI site within the Protease PFUS encoding region were synthesized (the base sequences of the primers SUB3 and NPR-10 are shown in the SEQ ID NOS:26 and 27 of the Sequence Listing, respectively).

PCR reaction mixtures each of which containing the plasmid pNAPS1 as a template and a combination of the primers SPOF0 and NPR-10 or a combination of the primers SUB3 and SPOR0 were prepared and subjected to 20 cycles of reactions of 94° C. for 30 seconds—50° C. for 1 munute—72° C. for 1 minute. DNA fragments of approximately 0.13 kb and approximately 0.35 kb amplified in the two reaction mixtures were mixed together, denatured at 94° C. for 10 minutes, cooled gradually to 37° C. to form a heteroduplex. A double-stranded DNA was then generated from the heteroduplex by means of Taq polymerase (Takara Shuzo). A PCR reaction mixture containing the double-stranded DNA thus obtained as a template and the primers SUB3 and NPR-10 was prepared and subjected to 25 cycles of reactions of 94° C. for 30 seconds—50° C. for 1 minute—72° C. for 1 minute. A DNA fragment obtained by digesting the amplified DNA fragment of approximately 0.43 kb with BamHI and SpeI (Takara Shuzo) was mixed and ligated with the plasmid pSNP2 that had been digested with BamHI and SpeI. The reaction mixture was used to transform *Bacillus subtilis* DB104.

Resulting kanamycin-resistant transformants were inoculated on skim milk plates (LB-agar medium for high temperature cultivation containing 10 μg/mL of kanamycin and 1% skim milk) to form colonies. Subsequently, the plates were incubated at 70° C. and the protease activities expressed by the respective transformants were examined based on the degree of degradation of the skim milk around the colonies. As a result, one clone that exhibited a particularly high activity was isolated and a plasmid, which was designated as the plasmid pSPO124, was prepared from the clone. *Bacillus subtilis* DB104 transformed with this plasmid was designated as *Bacillus subtilis* DB104/pSPO124. The base sequence of the plasmid pSPO124 was analyzed, and it was found that the base sequence which encodes Ser in the plasmid pNAPS1 was substituted by a base sequence GGGAAT, that is, that a protein in which Ser was changed to two amino acid residues Gly-Asn was encoded. Additionally, it proved that the 25th codon from the initiation codon corresponding to Pro (CCA) of the Protease PFUS gene was changed to a codon encoding Leu (CTA) simultaneously with the mutation as described above.

(7) Construction of the Protease Expression Plasmid pNAPSΔC

A termination codon was introduced on the C-terminal side of the 544th amino acid residue from the initiation codon of the Protease PFUS gene in the plasmid pNAPS1 to construct a plasmid which expresses a protease lacking downstream from this site. The primer NPR544 which introduces a termination codon (base sequence: TGA) on the C-terminal side of the codon encoding the 544th amino acid residue in the gene and has an SphI site was synthesized (the base sequence of the primer NPR544 is shown in the SEQ ID NO:28 of the Sequence Listing). In addition, the primer NPFE81 was synthesized based on the base sequence of the portion upstream from the NspV site in the gene (the base sequence of the primer NPFE81 is shown in the SEQ ID NO:29 of the Sequence Listing).

A PCR reaction mixture containing the plasmid pNAPS1 as a template and the primers NPFE81 and NPR544 was prepared and subjected to 20 cycles of reactions of 94° C. for 30 seconds—50° C. for 1 minute—72° C. for 1 minute. The amplified DNA fragment of approximately 0.61 kb was digested with NspV (Takara Shuzo) and SpeI to obtain a DNA fragment of approximately 0.13 kb containing the termination codon. This DNA fragment was mixed and ligated with the plasmid pNAPS1 that had been digested with restriction enzymes NspV and SphI. The reaction mixture was used to transform *Bacillus subtilis* DB104. Plasmids were prepared from the resulting kanamycin-resistant transformants, a plasmid into which the DNA fragment of approximately 0.13 kb was inserted was selected and designated as the plasmid pNAPSΔC. *Bacillus subtilis* DB104 transformed with the plasmid pNAPSΔC was designated as *Bacillus subtilis* DB104/pNAPSΔC.

(8) Construction of the Protease Expression Plasmid pSPO124ΔC

A DNA fragment of approximately 1.3 kb obtained by digesting the plasmid pNAPSΔC with NspV and SphI was isolated, then mixed and ligated with the plasmid pSPO124 that had been digested with NspV and SphI. The reaction mixture was used to transform *Bacillus subtilis* DB104. Plasmids were prepared from the resulting kanamycin-resistant transformants, a plasmid into which the DNA fragment of approximately 1.3 kb was inserted was selected and designated as the plasmid pSPO124ΔC. *Bacillus subtilis* DB104 transformed with the plasmid pSPO124ΔC was designated as *Bacillus subtilis* DB104/pSPO124ΔC.

EXAMPLE 3

(1) Cultivation of *Bacillus subtilis* Transformed with a Plasmid Containing the Protease PFUS Gene and preparation of a crude enzyme solution.

*Bacillus subtilis* DB104/pNAPS1, which is *Bacillus subtilis* DB104 into which the plasmid pNAPS1 containing the Protease PFUS gene was introduced as described in Example 2, was cultured in 2 mL of LB medium (Tryptone 10 g/L, yeast extract 5 g/L, NaCl 5 g/L, pH 7.2) containing 10 μg/mL of kanamycin at 37° C. for 24 hours. The culture was centrifuged to obtain a culture supernatant (the preparation 1-S) and cells.

The cells were suspended in 100 μL of 50 mM Tris-HCl, pH 7.5 and digested at 37° C. for 45 minutes after an addition of 2 mg of lysozyme (Sigma). The digested sample was heat-treated at 95° C. for 10 minutes, and then a supernatant was collected by centrifugation to obtain a cell-free extract (the preparation 1-L).

Similarly, culture supernatants and cell-free extracts were obtained from Bacillus subtilis DB104/pSPO124 containing the plasmid pSPO124, Bacillus subtilis DB104/pNAPSΔC containing the plasmid pNAPSΔC or Bacillus subtilis DB104/pSPO124ΔC containing the plasmid pSPO124ΔC. The culture supernatant and the cell-free extract from Bacillus subtilis DB104/pSPO124 were designated as 124-S and 124-L, respectively. The culture supernatant and the cell-free extract from Bacillus subtilis DB104/pNAPSΔC were designated as ΔC-S and ΔC-L, respectively. The culture supernatant and the cell-free extract from Bacillus subtilis DB104/pSPO124ΔC were designated as 124ΔC-S and 124ΔC-L, respectively. Protease activities were determined with these preparations and the concentration of the protease contained in each preparation was determined.

(2) Comparison of Protease Productivities

The activity of Protease PFUS was determined by spectroscopically measuring the amount of p-nitroaniline generated in an enzymatic hydrolysis reaction using Suc-Ala-Ala-Pro-Phe-p-NA (Sigma) (SEQ ID NO:33) as a substrate. Briefly, an enzyme preparation to be measured for its enzymatic activity was appropriately diluted. 50 μL of 1 mM Suc-Ala-Ala-Pro-Phe-p-NA (SEQ ID NO:33) solution in 100 mM phosphate buffer, pH 7.0 was added to 50 μL of the diluted sample solution. Then, the reaction was allowed to proceed at 95° C. for 30 minutes. After terminating the reaction by cooling on ice, absorbance at 405 nm was measured to calculate the amount of p-nitroaniline generated. One unit of the enzyme was defined as the amount of the enzyme which generated 1 μmole of p-nitroaniline per 1 minute at 95° C. The amount of enzyme protein expressed in the culture supernatant or the cells was calculated based on the measured enzymatic activity assuming the specific activity as 9.5 unit/mg protein of Protease PFUS.

The protease activity of each enzyme preparation prepared in Example 3-(1) was measured. The productivity of Protease PFUS per 1 L of culture of each transformant calculated from the measurement is shown in Table 1.

In Bacillus subtilis DB104/pSPO124, the productivity of Protease PFUS in the cells increased by 3.6. fold as compared with that of Bacillus subtilis DB104/pNAPS1. In Bacillus subtilis DB104/pNAPSΔC, the productivity of Protease PFUS increased in the culture supernatant by 2.4 fold and in the cells by 2.2 fold, respectively. Also, in Bacillus subtilis DB104/pSPO124ΔC, the productivity of Protease PFUS increased in the culture supernatant by 2 fold and in the cells by 2.4 fold, respectively. The productivity per cells also increased.

The total amount of Protease PFUS produced in the culture supernatant and the cells increased by 2.1 fold for Bacillus subtilis DB104/pSPO124, by 2.1 fold for Bacillus subtilis DB104/pNAPSΔC and by 2.2 fold for Bacillus subtilis DB104/pSPO124ΔC, respectively, as compared with that of Bacillus subtilis DB104/pNAPS1.

TABLE 1

The productivity of Protease PFUS (mg/L of culture)

| Transformant (Plasmid) | Culture Supernatant | Cells | Culture Supernatant + Cells |
|---|---|---|---|
| pNAPS1 | 15.1 | 12.5 | 27.6 |
| pSPO124 | 13.1 | 45.4 | 58.5 |
| pNAPSΔC | 35.5 | 28.1 | 63.6 |
| pSPO124ΔC | 30.5 | 30.1 | 60.6 |

EXAMPLE 4

(1) Preparation of Purified Enzyme Preparation of the Mature Protease PFUS

Bacillus subtilis DB104/pNAPS1 and Bacillus subtilis DB104/pSPO124ΔC, both of which are Bacillus subtilis DB104 into which the gene for the hyperthermostable protease of the present invention was introduced as described in Example 2, were separately inoculated into 5 mL of LB medium containing 10 μg/mL kanamycin and cultured with shaking at 37° C. for 7 hours. The cultures of 5 mL were inoculated into 500 mL of TM medium (soybean powder 5 g/L, Polypeptone 10 g/L, meat extract 5 g/L, yeast extract 2 g/L, glucose 10 g/L, $FeSO_4 \cdot 7H_2O$ 10 mg/L, $MnSO_4 \cdot 4H_2O$ 10 mg/L, $ZnSO_4 \cdot 7H_2O$ 1 mg/L, pH 7.0) containing 10 μg/mL of kanamycin in 5 L Erlenmeyer flasks and cultured with shaking at 30° C. for 3 days. The resulting cultures were sonicated, heat-treated at 95° C. for 30 minutes, then centrifuged to collect supernatants. Ammonium sulfate was added to the supernatants to 25% saturation, then the supernatants obtained by subsequent centrifugation were applied to Micro-Prep Methyl HIC columns (Bio-Rad) equilibrated with 25 mM Tris-HCl buffer (pH 7.6) containing 25% saturated ammonium sulfate. After washing the gel with the same buffer, Protease PFUS adsorbed to the columns was eluted by stepwise elution using 25 mM Tris-HCl buffer (pH 7.6) containing 40% ethanol. The fractions containing Protease PFUS thus obtained were subjected to gel filtration using NAP-25 columns (Pharmacia) equilibrated with 0.05% trifluoroacetic acid containing 20% acetonitrile, desalted while denaturing Protease PFUS, then purified preparations of Protease PFUS were obtained. The preparations obtained from Bacillus subtilis DB104/pNAPS1 and Bacillus subtilis DB104/pSPO124ΔC were designated as NAPS-1 and SPO-124ΔC, respectively.

Electrophoresis of both of the purified enzyme preparations on 0.1% SDS-10% polyacrylamide gel followed by staining with Coomassie Brilliant Blue R-250 revealed single bands for both of the purified enzyme preparations NAPS-1 and SPO-124ΔC with an estimated molecular weight of approximately 45 kDa.

(2) Analysis of the N-Terminal Amino Acid Sequence of the Mature Protease PFUS

N-terminal amino acid sequences of the purified enzyme preparations NAPS-1 and SPO-124ΔC were analyzed by automated Edman method using G1000A protein sequencer (Hewlett-Packard). Both of the N-terminal amino acid sequences of the two purified enzyme preparations were as shown in the SEQ ID NO:22 of the Sequence Listing. This sequence coincides with the sequence from position 133 to position 144 of the amino acid sequence of Protease PFUS as shown in the SEQ ID NO:16 of the Sequence Listing, indicating that both of NAPS-1 and SPO-124ΔC are enzymes consisting of a polypeptide starting from this portion.

(3) Mass Spectrometric Analysis of the Mature Protease PFUS

Mass spectrometric analysis on the purified enzyme preparations NAPS-1 and SPO-124ΔC was carried out using API300 quadrupole triple mass spectrometer (Perkin-Elmer Sciex) Based on the estimated molecular weight of NAPS-1, 43,744 Da, it was demonstrated that the mature Protease PEUS produced by *Bacillus subtilis* DB104/pNAPS1 is an enzyme consisting of a polypeptide from Ala at position 133 to Thr at position 552 of the amino acid sequence of Protease PFUS as shown in the SEQ ID NO:16 of the Sequence Listing. Furthermore, based on the estimated molecular weight of SPO-124ΔC, 42,906 Da, it was demonstrated that the mature Protease PEUS produced by *Bacillus subtilis* DB104/pSPO124ΔC is an enzyme consisting of a polypeptide from Ala at position 133 to Ser at position 544 of the amino acid sequence of Protease PFUS as shown in the SEQ ID NO:16 of the Sequence Listing, i.e., the amino acid sequence as shown in the SEQ ID NO:1 of the Sequence Listing.

What is claimed is:

1. An isolated polynucleotide encoding an amino acid sequence according to formula I:

SIG-(SEQ ID NO:30)-PRO [I]

wherein SIG represents the amino acid sequence SEQ ID NO:3 of a signal peptide derived from a subtilisin, PRO represents the amino acid sequence of a protease consisting of an amino acid sequence in which one or more amino acid residues are deleted from the C-terminus of the amino acid sequence of SEQ ID NO:4 and having a protease activity, wherein said protease amino acid sequence comprises the amino acid sequence of SEQ ID NO:1.

2. The polynucleotide according to claim 1, which is contained in the plasmid pSPO124ΔC.

3. A method of producing a protease of interest, comprising:
   culturing a bacterium of genus *Bacillus* into which the polynucleotide according to claim 1 is introduced; and collecting said protease from the culture.

4. The method of producing a protease according to claim 3, wherein the bacterium of genus *Bacillus* is *Bacillus subtilis*.

5. The method of producing a protease according to claim 3, wherein the polynucleotide is introduced into the bacterium of genus *Bacillus* by means of a plasmid vector.

6. The method of producing a protease according to claim 5, wherein the plasmid pSPO124ΔC is introduced into the bacterium of genus *Bacillus*.

7. The method of producing a protease according to claim 5, comprising culturing *Bacillus subtilis* DB104/pSPO124ΔC FERM BP-6294, and collecting the protein of interest from the culture.

8. A plasmid vector into which the polynucleotide according to claim 1 is inserted.

9. The plasmid vector according to claim 8, which is pSPO124ΔC.

* * * * *

SEQUENCE LISTING

<160> NUMBER OF SEQ ID NOS: 33

<210> SEQ ID NO 1
<211> LENGTH: 412
<212> TYPE: PRT
<213> ORGANISM: Pyrococcus furiosus

<400> SEQUENCE: 1

```
Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
                20                  25                  30

Ile Asp Thr Gly Ile Asp Ala Ser His Pro Asp Leu Gln Gly Lys Val
            35                  40                  45

Ile Gly Trp Val Asp Phe Val Asn Gly Arg Ser Tyr Pro Tyr Asp Asp
        50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205

Arg Leu Lys Pro Glu Val Val Ala Pro Gly Asn Trp Ile Ile Ala Ala
        210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285
```

```
Asp Ile Ala Tyr Gly Ala Gly Arg Val Asn Ala Tyr Lys Ala Ile Asn
            290                 295                 300
Tyr Asp Asn Tyr Ala Lys Leu Val Phe Thr Gly Tyr Val Ala Asn Lys
305                 310                 315                 320
Gly Ser Gln Thr His Gln Phe Val Ile Ser Gly Ala Ser Phe Val Thr
                325                 330                 335
Ala Thr Leu Tyr Trp Asp Asn Ala Asn Ser Asp Leu Asp Leu Tyr Leu
            340                 345                 350
Tyr Asp Pro Asn Gly Asn Gln Val Asp Ser Tyr Thr Ala Tyr Tyr
            355                 360                 365
Gly Phe Glu Lys Val Gly Tyr Tyr Asn Pro Thr Asp Gly Thr Trp Thr
            370                 375                 380
Ile Lys Val Val Ser Tyr Ser Gly Ser Ala Asn Tyr Gln Val Asp Val
385                 390                 395                 400
Val Ser Asp Gly Ser Leu Ser Gln Pro Gly Ser Ser
                405                 410
```

<210> SEQ ID NO 2
<211> LENGTH: 1236
<212> TYPE: DNA
<213> ORGANISM: Artificial Sequence
<220> FEATURE:
<223> OTHER INFORMATION: Synthetic

<400> SEQUENCE: 2

```
gcagaattag aaggactgga tgagtctgca gctcaagtta tggcaactta cgtttggaac    60
ttgggatatg atggttctgg aatcacaata ggaataattg acactggaat tgacgcttct   120
catccagatc tccaaggaaa agtaattggg tgggtagatt ttgtcaatgg taggagttat   180
ccatacgatg accatggaca tggaactcat gtagcttcaa tagcagctgg tactggagca   240
gcaagtaatg caagtacaa gggaatggct ccaggagcta agctggcggg aattaaggtt   300
ctaggtgccg atggttctgg aagcatatct actataatta agggagttga gtgggccgtt   360
gataacaaaa ataagtacgg aattaaggtc attaatcttt ctcttggttc aagccagagc   420
tcagatggta ctgacgctct aagtcaggct gttaatgcag cgtgggatgc tggattagtt   480
gttgtggttg ccgctggaaa cagtggacct aacaagtata caatcggttc tccagcagct   540
gcaagcaaag ttattacagt tggagccgtt gacaagtatg atgttataac aagcttctca   600
agcagagggc caactgcaga cggcaggctt aagcctgagg ttgttgctcc aggaaactgg   660
ataattgctg ccagagcaag tggaactagc atgggtcaac caattaatga ctattacaca   720
gcagctcctg ggacatcaat ggcaactcct cacgtagctg gtattgcagc cctcttgctc   780
caagcacacc cgagctggac tccagacaaa gtaaaaacag ccctcataga aactgctgat   840
atcgtaaagc cagatgaaat agccgatata gcctacggtg caggtagggt taatgcatac   900
aaggctataa actacgataa ctatgcaaag ctagtgttca ctggatatgt tgccaacaaa   960
ggcagccaaa ctcaccagtt cgttattagc ggagcttcgt tcgtaactgc cacattatac  1020
tgggacaatg ccaatagcga ccttgatctt tacctctacg atcccaatgg aaaccaggtt  1080
gactactctt acaccgccta ctatggattc gaaaaggttg gttattacaa cccaactgat  1140
ggaacatgga caattaaggt tgtaagctac agcggaagtg caaactatca agtagatgtg  1200
gtaagtgatg gttccctttc acagcctgga agttca                             1236
```

<210> SEQ ID NO 3

```
<211> LENGTH: 29
<212> TYPE: PRT
<213> ORGANISM: Bacillus subtilis

<400> SEQUENCE: 3

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala
            20                  25

<210> SEQ ID NO 4
<211> LENGTH: 522
<212> TYPE: PRT
<213> ORGANISM: Pyrococcus furiosus
<220> FEATURE:
<221> NAME/KEY: misc_feature
<222> LOCATION: (428)..(428)
<223> OTHER INFORMATION: Xaa at position 428 is Gly or Val.

<400> SEQUENCE: 4

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val
        35                  40                  45

Ile Gly Trp Val Asp Phe Val Asn Gly Arg Ser Tyr Pro Tyr Asp Asp
    50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205

Arg Leu Lys Pro Glu Val Val Ala Pro Gly Asn Trp Ile Ile Ala Ala
    210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
```

```
                290                 295                 300
Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350

Tyr Asp Pro Asn Gly Asn Gln Val Asp Tyr Ser Tyr Thr Ala Tyr Tyr
        355                 360                 365

Gly Phe Glu Lys Val Gly Tyr Tyr Asn Pro Thr Asp Gly Thr Trp Thr
370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser Pro Ser Pro Gln
                405                 410                 415

Pro Glu Pro Thr Val Asp Ala Lys Thr Phe Gln Xaa Ser Asp His Tyr
            420                 425                 430

Tyr Tyr Asp Arg Ser Asp Thr Phe Thr Met Thr Val Asn Ser Gly Ala
        435                 440                 445

Thr Lys Ile Thr Gly Asp Leu Val Phe Asp Thr Ser Tyr His Asp Leu
450                 455                 460

Asp Leu Tyr Leu Tyr Asp Pro Asn Gln Lys Leu Val Asp Arg Ser Glu
465                 470                 475                 480

Ser Pro Asn Ser Tyr Glu His Val Glu Tyr Leu Thr Pro Ala Pro Gly
                485                 490                 495

Thr Trp Tyr Phe Leu Val Tyr Ala Tyr Tyr Thr Tyr Gly Trp Ala Tyr
            500                 505                 510

Tyr Glu Leu Thr Ala Lys Val Tyr Tyr Gly
        515                 520

<210> SEQ ID NO 5
<211> LENGTH: 4765
<212> TYPE: DNA
<213> ORGANISM: Artificial Sequence
<220> FEATURE:
<223> OTHER INFORMATION: Synthetic

<400> SEQUENCE: 5
tttaaattat aagatataat cactccgagt gatgagtaag atacatcatt acagtcccaa      60
aatgtttata attggaacgc agtgaatata caaaatgaat ataacctcgg aggtgactgt     120
agaatgaata agaagggact tactgtgcta tttatagcga taatgctcct ttcagtagtt     180
ccagtgcact ttgtgtccgc agaaacacca ccggttagtt cagaaaattc aacaacttct     240
atactcccta accaacaagt tgtgacaaaa gaagtttcac aagcggcgct taatgctata     300
atgaaaggac aacccaacat ggttcttata atcaagacta aggaaggcaa acttgaagag     360 gcaaaaccg agcttgaaaa gctaggtgca gagattcttg acgaaaatag agttcttaac      420
atgttgctag ttaagattaa gcctgagaaa gttaaagagc tcaactatat ctcatctctt     480 gaaaagcct ggcttaacag agaagttaag ctttccccctc caattgtcga aaggacgtc     540 aagactaagg agccctccct agaaccaaaa atgtataaca gcacctgggt aattaatgct    600
ctccagttca tccaggaatt tggatatgat ggtagtggtg ttgttgttgc agtacttgac     660
acgggagttg atccgaacca tcctttcttg agcataactc cagatggacg caggaaaatt     720
atagaatgga aggattttac agacgaggga ttcgtggata catcattcag ctttagcaag     780
```

-continued

```
gttgtaaatg ggactcttat aattaacaca acattccaag tggcctcagg tctcacgctg    840
aatgaatcga caggacttat ggaatacgtt gttaagactg tttacgtgag caatgtgacc    900
attgaaaata tcacttctgc taatggcatc tatcacttcg gcctgctccc agaaagatac    960
ttcgacttaa acttcgatgg tgatcaagag gacttctatc ctgtcttatt agttaactcc   1020
actggcaatg gttatgacat tgcatatgtg gatactgacc ttgactacga cttcaccgac   1080
gaagttccac ttggccagta caacgttact tatgatgttg ctgtttttag ctactactac   1140
ggtcctctca actacgtgct tgcagaaata gatcctaacg gagaatatgc agtatttggg   1200
tgggatggtc acggtcacgg aactcacgta gctggaactg ttgctggtta cgacagcaac   1260
aatgatgctt gggattggct cagtatgtac tctggtgaat gggaagtgtt ctcaagactc   1320
tatggttggg attatacgaa cgttaccaca gacaccgtgc agggtgttgc tccaggtgcc   1380
caaataatgg caataagagt tcttaggagt gatggacggg gtagcatgtg ggatattata   1440
gaaggtatga catacgcagc aacccatggt gcagacgtta taagcatgag tctcggtgga   1500
aatgctccat acttagatgg tactgatcca gaaagcgttg ctgtggatga gcttaccgaa   1560
aagtacggtg ttgtattcgt aatagctgca ggaaatgaag gtcctggcat taacatcgtt   1620
ggaagtcctg gtgttgcaac aaaggcaata actgttggag ctgctgcagt gcccattaac   1680
gttggagttt atgtttccca agcacttgga tatcctgatt actatggatt ctattacttc   1740
cccgcctaca caaacgttag aatagcattc ttctcaagca gagggccgag aatagatggt   1800
gaaataaaac ccaatgtagt ggctccaggt tacggaattt actcatccct gccgatgtgg   1860
attggcggag ctgacttcat gtctggaact tcgatggcta ctccacatgt cagcggtgtc   1920
gttgcactcc tcataagcgg ggcaaaggcc gaggaatat actacaatcc agatataatt   1980
aagaaggttc ttgagagcgg tgcaacctgg cttgagggag atccatatac tgggcagaag   2040
tacactgagc ttgaccaagg tcatggtctt gttaacgtta ccaagtcctg ggaaatcctt   2100
aaggctataa acggcaccac tctcccaatt gttgatcact gggcagacaa gtcctacagc   2160
gactttgcgg agtactggg tgtggacgtt ataagaggtc tctacgcaag gaactctata   2220
cctgacattg tcgagtggca cattaagtac gtaggggaca cggagtacag aacttttgag   2280
atctatgcaa ctgagccatg gattaagcct tttgtcagtg gaagtgtaat tctagagaac   2340
aataccgagt ttgtccttag ggtgaaatat gatgtagagg gtcttgagcc aggtctctat   2400
gttgaaagga taatcattga tgatccaaca acgccagtta ttgaagacga gatcttgaac   2460
acaattgtta ttcccgagaa gttcactcct gagaacaatt acaccctcac ctggtatgat   2520
attaatggtc cagaaatggt gactcaccac ttcttcactg tgcctgaggg agtggacgtt   2580
ctctacgcga tgaccacata ctgggactac ggtctgtaca gaccagatgg aatgttttgtg   2640 ttcccatacc agctagatta tcttcccgct gcagtctcaa atccaatgcc tggaaactgg   2700
gagctagtat ggactggatt taactttgca cccctctatg agtcgggctt ccttgtaagg   2760
atttacggag tagagataac tccaagcgtt tggtacatta acaggacata ccttgacact   2820
aacactgaat tctcaattga attcaatatt actaacatct atgccccaat taatgcaact   2880
ctaatcccca ttggccttgg aacctacaat gcgagcgttg aaagcgttgg tgatggagag   2940
ttcttcataa aggcattga agttcctgaa ggcaccgcag agttgaagat taggataggc   3000
aacccaagtg ttccgaattc agatctagac ttgtaccttt atgacagtaa aggcaattta   3060
gtggccttag atggaaaccc aacagcagaa gaagaggttg tagttgagta tcctaagcct   3120
```

-continued

```
ggagtttatt caatagtagt acatggttac agcgtcaggg acgaaaatgg taatccaacg    3180
acaaccacct ttgacttagt tgttcaaatg acccttgata atggaaacat aaagcttgac    3240
aaagactcga ttattcttgg aagcaatgaa agcgtagttg taactgcaaa cataacaatt    3300
gatagagatc atcctacagg agtatactct ggtatcatag agattagaga taatgaggtc    3360
taccaggata caaatacttc aattgcgaaa atacccataa ctttggtaat tgacaaggcg    3420
gactttgccg ttggtctcac accagcagag ggagtacttg gagaggctag aaattacact    3480
ctaattgtaa agcatgccct aacactagag cctgtgccaa atgctacagt gattatagga    3540
aactacacct acctcacaga cgaaaacggt acagtgacat tcacgtatgc tccaactaag    3600
ttaggcagtg atgaaatcac agtcatagtt aagaaagaga acttcaacac attagagaag    3660
accttccaaa tcacagtatc agagcctgaa ataactgaag aggacataaa tgagcccaag    3720
cttgcaatgt catcaccaga agcaaatgct accatagtat cagttgagat ggagagtgag    3780
ggtggcgtta aaagacagt gacagtgaa ataactataa acggaaccgc taatgagact     3840
gcaacaatag tggttcctgt tcctaagaag gccgaaaaca tcgaggtaag tggagaccac    3900
gtaatttcct atagtataga ggaaggagag tacgccaagt acgttataat tacagtgaag    3960
tttgcatcac ctgtaacagt aactgttact tacactatct atgctggccc aagagtctca    4020
atcttgacac ttaacttcct tggctactca tggtacagac tatattcaca gaagtttgac    4080
gaattgtacc aaaaggccct tgaattggga gtggacaacg agacattagc tttagccctc    4140
agctaccatg aaaagccaa agagtactac gaaaaggccc ttgagcttag cgagggtaac    4200
ataatccaat accttggaga cataagacta ttacctccat taagacaggc atacatcaat    4260
gaaatgaagg cagttaagat actgaaaag gccatagaag aattagaggg tgaagagtaa    4320
tctccaattt ttcccacttt ttcttttata acattccaag ccttttctta gcttcttcgc    4380
tcattctatc aggagtccat ggaggatcaa aggtaagttc aacctccaca tctcttactc    4440
ctgggatttc gagtactttc tcctctacag ctctaagaag ccagagagtt aaaggacacc    4500
caggagttgt cattgtcatc tttatatata ccgttttgtc aggattaatc tttagctcat    4560
aaattaatcc aaggtttaca acatccatcc caatttctgg gtcgataacc tcctttagct    4620
tttccagaat catttcttca gtaatttcaa ggttctcatc tttggtttct ctcacaaacc    4680
caatttcaac ctgcctgata ccttctaact ccctaagctt gttatatatc tccaaaagag    4740
tggcatcatc aattttctct ttaaa                                          4765
```

<210> SEQ ID NO 6
<211> LENGTH: 1398
<212> TYPE: PRT
<213> ORGANISM: Pyrococcus furiosus

<400> SEQUENCE: 6

```
Met Asn Lys Lys Gly Leu Thr Val Leu Phe Ile Ala Ile Met Leu Leu
1               5                   10                  15

Ser Val Val Pro Val His Phe Val Ser Ala Glu Thr Pro Val Ser
            20                  25                  30

Ser Glu Asn Ser Thr Thr Ser Ile Leu Pro Asn Gln Gln Val Val Thr
        35                  40                  45

Lys Glu Val Ser Gln Ala Ala Leu Asn Ala Ile Met Lys Gly Gln Pro
    50                  55                  60

Asn Met Val Leu Ile Ile Lys Thr Lys Glu Gly Lys Leu Glu Glu Ala
65                  70                  75                  80
```

-continued

```
Lys Thr Glu Leu Glu Lys Leu Gly Ala Glu Ile Leu Asp Glu Asn Arg
                85              90              95

Val Leu Asn Met Leu Leu Val Lys Ile Lys Pro Glu Lys Val Lys Glu
            100             105             110

Leu Asn Tyr Ile Ser Ser Leu Glu Lys Ala Trp Leu Asn Arg Glu Val
        115             120             125

Lys Leu Ser Pro Pro Ile Val Glu Lys Asp Val Lys Thr Lys Glu Pro
130             135             140

Ser Leu Glu Pro Lys Met Tyr Asn Ser Thr Trp Val Ile Asn Ala Leu
145             150             155             160

Gln Phe Ile Gln Glu Phe Gly Tyr Asp Gly Ser Gly Val Val Val Ala
                165             170             175

Val Leu Asp Thr Gly Val Asp Pro Asn His Pro Phe Leu Ser Ile Thr
            180             185             190

Pro Asp Gly Arg Arg Lys Ile Ile Glu Trp Lys Asp Phe Thr Asp Glu
            195             200             205

Gly Phe Val Asp Thr Ser Phe Ser Phe Ser Lys Val Val Asn Gly Thr
        210             215             220

Leu Ile Ile Asn Thr Thr Phe Gln Val Ala Ser Gly Leu Thr Leu Asn
225             230             235             240

Glu Ser Thr Gly Leu Met Glu Tyr Val Val Lys Thr Val Tyr Val Ser
                245             250             255

Asn Val Thr Ile Gly Asn Ile Thr Ser Ala Asn Gly Ile Tyr His Phe
            260             265             270

Gly Leu Leu Pro Glu Arg Tyr Phe Asp Leu Asn Phe Asp Gly Asp Gln
        275             280             285

Glu Asp Phe Tyr Pro Val Leu Leu Val Asn Ser Thr Gly Asn Gly Tyr
    290             295             300

Asp Ile Ala Tyr Val Asp Thr Asp Leu Asp Tyr Asp Phe Thr Asp Glu
305             310             315             320

Val Pro Leu Gly Gln Tyr Asn Val Thr Tyr Asp Val Ala Val Phe Ser
                325             330             335

Tyr Tyr Tyr Gly Pro Leu Asn Tyr Val Leu Ala Glu Ile Asp Pro Asn
            340             345             350

Gly Glu Tyr Ala Val Phe Gly Trp Asp Gly His Gly His Gly Thr His
        355             360             365

Val Ala Gly Thr Val Ala Gly Tyr Asp Ser Asn Asn Asp Ala Trp Asp
    370             375             380

Trp Leu Ser Met Tyr Ser Gly Glu Trp Glu Val Phe Ser Arg Leu Tyr
385             390             395             400

Gly Trp Asp Tyr Thr Asn Val Thr Thr Asp Thr Val Gln Gly Val Ala
                405             410             415

Pro Gly Ala Gln Ile Met Ala Ile Arg Val Leu Arg Ser Asp Gly Arg
            420             425             430

Gly Ser Met Trp Asp Ile Ile Glu Gly Met Thr Tyr Ala Ala Thr His
        435             440             445

Gly Ala Asp Val Ile Ser Met Ser Leu Gly Gly Asn Ala Pro Tyr Leu
    450             455             460

Asp Gly Thr Asp Pro Glu Ser Val Ala Val Asp Glu Leu Thr Glu Lys
465             470             475             480

Tyr Gly Val Val Phe Val Ile Ala Ala Gly Asn Glu Gly Pro Gly Ile
                485             490             495

Asn Ile Val Gly Ser Pro Gly Val Ala Thr Lys Ala Ile Thr Val Gly
```

-continued

```
                500                     505                     510
    Ala Ala Ala Val Pro Ile Asn Val Gly Val Tyr Val Ser Gln Ala Leu
                515                     520                     525

Gly Tyr Pro Asp Tyr Tyr Gly Phe Tyr Tyr Phe Pro Ala Tyr Thr Asn
                530                     535                     540

Val Arg Ile Ala Phe Phe Ser Ser Arg Gly Pro Arg Ile Asp Gly Glu
545                     550                     555                     560

Ile Lys Pro Asn Val Val Ala Pro Gly Tyr Gly Ile Tyr Ser Ser Leu
                565                     570                     575

Pro Met Trp Ile Gly Gly Ala Asp Phe Met Ser Gly Thr Ser Met Ala
                580                     585                     590

Thr Pro His Val Ser Gly Val Val Ala Leu Leu Ile Ser Gly Ala Lys
                595                     600                     605

Ala Glu Gly Ile Tyr Tyr Asn Pro Asp Ile Ile Lys Lys Val Leu Glu
                610                     615                     620

Ser Gly Ala Thr Trp Leu Glu Gly Asp Pro Tyr Thr Gly Gln Lys Tyr
625                     630                     635                     640

Thr Glu Leu Asp Gln Gly His Gly Leu Val Asn Val Thr Lys Ser Trp
                645                     650                     655

Glu Ile Leu Lys Ala Ile Asn Gly Thr Thr Leu Pro Ile Val Asp His
                660                     665                     670

Trp Ala Asp Lys Ser Tyr Ser Asp Phe Ala Glu Tyr Leu Gly Val Asp
                675                     680                     685

Val Ile Arg Gly Leu Tyr Ala Arg Asn Ser Ile Pro Asp Ile Val Glu
                690                     695                     700

Trp His Ile Lys Tyr Val Gly Asp Thr Glu Tyr Arg Thr Phe Glu Ile
705                     710                     715                     720

Tyr Ala Thr Glu Pro Trp Ile Lys Pro Phe Val Ser Gly Ser Val Ile
                725                     730                     735

Leu Glu Asn Asn Thr Glu Phe Val Leu Arg Val Lys Tyr Asp Val Glu
                740                     745                     750

Gly Leu Glu Pro Gly Leu Tyr Val Gly Arg Ile Ile Asp Asp Pro
                755                     760                     765

Thr Thr Pro Val Ile Glu Asp Glu Ile Leu Asn Thr Ile Val Ile Pro
                770                     775                     780

Glu Lys Phe Thr Pro Glu Asn Asn Tyr Thr Leu Thr Trp Tyr Asp Ile
785                     790                     795                     800

Asn Gly Pro Glu Met Val Thr His His Phe Phe Thr Val Pro Glu Gly
                805                     810                     815

Val Asp Val Leu Tyr Ala Met Thr Thr Tyr Trp Asp Tyr Gly Leu Tyr
                820                     825                     830

Arg Pro Asp Gly Met Phe Val Phe Pro Tyr Gln Leu Asp Tyr Leu Pro
                835                     840                     845

Ala Ala Val Ser Asn Pro Met Pro Gly Asn Trp Glu Leu Val Trp Thr
                850                     855                     860

Gly Phe Asn Phe Ala Pro Leu Tyr Glu Ser Gly Phe Leu Val Arg Ile
865                     870                     875                     880

Tyr Gly Val Glu Ile Thr Pro Ser Val Trp Tyr Ile Asn Arg Thr Tyr
                885                     890                     895

Leu Asp Thr Asn Thr Glu Phe Ser Ile Glu Phe Asn Ile Thr Asn Ile
                900                     905                     910

Tyr Ala Pro Ile Asn Ala Thr Leu Ile Pro Ile Gly Leu Gly Thr Tyr
                915                     920                     925
```

-continued

```
Asn Ala Ser Val Glu Ser Val Gly Asp Gly Glu Phe Phe Ile Lys Gly
        930                 935                 940

Ile Glu Val Pro Glu Gly Thr Ala Glu Leu Lys Ile Arg Ile Gly Asn
945                 950                 955                 960

Pro Ser Val Pro Asn Ser Asp Leu Asp Leu Tyr Leu Tyr Asp Ser Lys
                965                 970                 975

Gly Asn Leu Val Ala Leu Asp Gly Asn Pro Thr Ala Glu Glu Val
            980                 985                 990

Val Val Glu Tyr Pro Lys Pro Gly Val Tyr Ser Ile Val Val His Gly
        995                 1000                1005

Tyr Ser Val Arg Asp Glu Asn Gly Asn Pro Thr Thr Thr Thr Phe
    1010                1015                1020

Asp Leu Val Val Gln Met Thr Leu Asp Asn Gly Asn Ile Lys Leu
    1025                1030                1035

Asp Lys Asp Ser Ile Ile Leu Gly Ser Asn Glu Ser Val Val Val
    1040                1045                1050

Thr Ala Asn Ile Thr Ile Asp Arg Asp His Pro Thr Gly Val Tyr
    1055                1060                1065

Ser Gly Ile Ile Glu Ile Arg Asp Asn Glu Val Tyr Gln Asp Thr
    1070                1075                1080

Asn Thr Ser Ile Ala Lys Ile Pro Ile Thr Leu Val Ile Asp Lys
    1085                1090                1095

Ala Asp Phe Ala Val Gly Leu Thr Pro Ala Glu Gly Val Leu Gly
    1100                1105                1110

Glu Ala Arg Asn Tyr Thr Leu Ile Val Lys His Ala Leu Thr Leu
    1115                1120                1125

Glu Pro Val Pro Asn Ala Thr Val Ile Ile Gly Asn Tyr Thr Tyr
    1130                1135                1140

Leu Thr Asp Glu Asn Gly Thr Val Thr Phe Thr Tyr Ala Pro Thr
    1145                1150                1155

Lys Leu Gly Ser Asp Glu Ile Thr Val Ile Val Lys Lys Glu Asn
    1160                1165                1170

Phe Asn Thr Leu Glu Lys Thr Phe Gln Ile Thr Val Ser Glu Pro
    1175                1180                1185

Glu Ile Thr Glu Glu Asp Ile Asn Glu Pro Lys Leu Ala Met Ser
    1190                1195                1200

Ser Pro Glu Ala Asn Ala Thr Ile Val Ser Val Glu Met Glu Ser
    1205                1210                1215

Glu Gly Gly Val Lys Lys Thr Val Thr Val Glu Ile Thr Ile Asn
    1220                1225                1230

Gly Thr Ala Asn Glu Thr Ala Thr Ile Val Val Pro Val Pro Lys
    1235                1240                1245

Lys Ala Glu Asn Ile Glu Val Ser Gly Asp His Val Ile Ser Tyr
    1250                1255                1260

Ser Ile Glu Glu Gly Glu Tyr Ala Lys Tyr Val Ile Ile Thr Val
    1265                1270                1275

Lys Phe Ala Ser Pro Val Thr Val Thr Val Thr Tyr Thr Ile Tyr
    1280                1285                1290

Ala Gly Pro Arg Val Ser Ile Leu Thr Leu Asn Phe Leu Gly Tyr
    1295                1300                1305

Ser Trp Tyr Arg Leu Tyr Ser Gln Lys Phe Asp Glu Leu Tyr Gln
    1310                1315                1320
```

| Lys | Ala | Leu | Glu | Leu | Gly | Val | Asp | Asn | Glu | Thr | Leu | Ala | Leu | Ala |
|---|---|---|---|---|---|---|---|---|---|---|---|---|---|---|
| 1325 | | | | 1330 | | | | | 1335 | | | | | |

| Leu | Ser | Tyr | His | Glu | Lys | Ala | Lys | Glu | Tyr | Tyr | Glu | Lys | Ala | Leu |
|---|---|---|---|---|---|---|---|---|---|---|---|---|---|---|
| 1340 | | | | | 1345 | | | | | 1350 | | | | |

| Glu | Leu | Ser | Glu | Gly | Asn | Ile | Ile | Gln | Tyr | Leu | Gly | Asp | Ile | Arg |
|---|---|---|---|---|---|---|---|---|---|---|---|---|---|---|
| 1355 | | | | | 1360 | | | | | 1365 | | | | |

| Leu | Leu | Pro | Pro | Leu | Arg | Gln | Ala | Tyr | Ile | Asn | Glu | Met | Lys | Ala |
|---|---|---|---|---|---|---|---|---|---|---|---|---|---|---|
| 1370 | | | | | 1375 | | | | | 1380 | | | | |

| Val | Lys | Ile | Leu | Glu | Lys | Ala | Ile | Glu | Glu | Leu | Glu | Gly | Glu | Glu |
|---|---|---|---|---|---|---|---|---|---|---|---|---|---|---|
| 1385 | | | | | 1390 | | | | | 1395 | | | | |

```
<210> SEQ ID NO 7
<211> LENGTH: 35
<212> TYPE: DNA
<213> ORGANISM: Artificial Sequence
<220> FEATURE:
<223> OTHER INFORMATION: Synthetic

<400> SEQUENCE: 7
ggwwsdrrtg ttrrhgthgc dgtdmtygac acbgg                        35

<210> SEQ ID NO 8
<211> LENGTH: 32
<212> TYPE: DNA
<213> ORGANISM: Artificial Sequence
<220> FEATURE:
<223> OTHER INFORMATION: Synthetic

<400> SEQUENCE: 8
kstcacggaa ctcacgtdgc bgghacdgtt gc                           32

<210> SEQ ID NO 9
<211> LENGTH: 33
<212> TYPE: DNA
<213> ORGANISM: Artificial Sequence
<220> FEATURE:
<223> OTHER INFORMATION: Synthetic

<400> SEQUENCE: 9
ascmgcaach gtkccvgcha cgtgagttcc gtg                          33

<210> SEQ ID NO 10
<211> LENGTH: 34
<212> TYPE: DNA
<213> ORGANISM: Artificial Sequence
<220> FEATURE:
<223> OTHER INFORMATION: Synthetic

<400> SEQUENCE: 10
chccgsyvac rtgbggagwd gccatbgavg tdcc                         34

<210> SEQ ID NO 11
<211> LENGTH: 1977
<212> TYPE: DNA
<213> ORGANISM: Artificial Sequence
<220> FEATURE:
<223> OTHER INFORMATION: Synthetic

<400> SEQUENCE: 11
atgaagaggt taggtgctgt ggtgctggca ctggtgctcg tgggtcttct ggccggaacg    60
gcccttgcgg cacccgtaaa accggttgtc aggaacaacg cggttcagca gaagaactac   120
ggactgctga ccccgggact gttcaagaaa gtccagagga tgaactggaa ccaggaagtg   180
```

-continued

```
gacaccgtca taatgttcgg gagctacgga gacagggaca gggcggttaa ggtactgagg    240
ctcatgggcg cccaggtcaa gtactcctac aagataatcc ctgctgtcgc ggttaaaata    300
aaggccaggg accttctgct gatcgcgggc atgatagaca cgggttactt cggtaacaca    360
agggtctcgg gcataaagtt catacaggag gattacaagg ttcaggttga cgacgccact    420
tccgtctccc agatagggc cgataccgtc tggaactccc tcggctacga cggaagcgt     480
gtggtggttg ccatcgtcga tacgggtata gacgcgaacc ccccgatct gaagggcaag    540
gtcataggct ggtacgacgc cgtcaacggc aggtcgaccc cctacgatga ccagggacac    600
ggaacccacg ttgcgggtat cgttgccgga accggcagcg ttaactccca gtacataggc    660
gtcgccccg gcgcgaagct cgtcggcgtc aaggttctcg gtgccgacgg ttcgggaagc    720
gtctccacca tcatcgcggg tgttgactgg gtcgtccaga acaaggacaa gtacgggata    780
agggtcatca acctctccct cggctcctcc cagagctccg acggaaccga ctccctcagt    840
caggccgtca caacgcctg gacgccggt atagtagtct gcgtcgccgc cggcaacagc    900
gggccgaaca cctacaccgt cggctcaccc gccgcgcga gcaaggtcat aaccgtcggt    960
gcagttgaca gcaacgacaa catcgccagc ttctccagca ggggaccgac cgcggacgga    1020
aggctcaagc cggaagtcgt cgcccccggc gttgacatca tagccccgcg cgccagcgga    1080
accagcatgg gcaccccgat aaacgactac tacaccaagg cctctggaac cagcatggcc    1140
accccgcacg tttcgggcgt tggcgcgctc atcctccagg cccacccgag ctggaccccg    1200
gacaaggtga agaccgccct catcgagacc gccgacatag tcgcccccaa ggagatagcg    1260
gacatcgcct acggtgcggg tagggtgaac gtctacaagg ccatcaagta cgacgactac    1320
gccaagctca ccttcaccgg ctccgtcgcc gacaagggaa cgccacccca cccttcgac    1380
gtcagcggcg ccaccttcgt gaccgccacc ctctactggg acacgggctc gagcgacatc    1440
gacctctacc tctacgaccc caacgggaac gaggttgact actcctacac cgcctactac    1500
ggcttcgaga aggtcggcta ctacaacccg accgccggaa cctggacggt caaggtcgtc    1560
agctacaagg gcgcggcgaa ctaccaggtc gacgtcgtca cgacgggag cctcagccag    1620
tccggcggcg gcaacccgaa tccaaacccc aaccgaacc caaccccgac caccgacacc    1680
cagaccttca ccggttccgt taacgactac tgggacacca cgacaccctt caccatgaac    1740
gtcaacagcg gtgccaccaa gataaccggt gacctgacct tcgatacttc ctacaacgac    1800
ctcgacctct acctctacga ccccaacggc aacctcgttg acaggtccac gtcgagcaac    1860
agctacgagc acgtcgagta cgccaacccc gccccgggaa cctggacgtt cctcgtctac    1920
gcctacagca cctacggctg ggcggactac cagctcaagg ccgtcgtcta ctacggg       1977
```

<210> SEQ ID NO 12
<211> LENGTH: 659
<212> TYPE: PRT
<213> ORGANISM: Thermococcus celer

<400> SEQUENCE: 12

```
Met Lys Arg Leu Gly Ala Val Val Leu Ala Leu Val Val Gly Leu
1               5                   10                  15

Leu Ala Gly Thr Ala Leu Ala Ala Pro Val Lys Pro Val Val Arg Asn
            20                  25                  30

Asn Ala Val Gln Gln Lys Asn Tyr Gly Leu Leu Thr Pro Gly Leu Phe
        35                  40                  45

Lys Lys Val Gln Arg Met Asn Trp Asn Gln Glu Val Asp Thr Val Ile
    50                  55                  60
```

```
Met Phe Gly Ser Tyr Gly Asp Arg Asp Arg Ala Val Lys Val Leu Arg
 65                  70                  75                  80

Leu Met Gly Ala Gln Val Lys Tyr Ser Tyr Lys Ile Ile Pro Ala Val
                 85                  90                  95

Ala Val Lys Ile Lys Ala Arg Asp Leu Leu Ile Ala Gly Met Ile
                100                 105                 110

Asp Thr Gly Tyr Phe Gly Asn Thr Arg Val Ser Gly Ile Lys Phe Ile
            115                 120                 125

Gln Glu Asp Tyr Lys Val Gln Val Asp Asp Ala Thr Ser Val Ser Gln
130                 135                 140

Ile Gly Ala Asp Thr Val Trp Asn Ser Leu Gly Tyr Asp Gly Ser Gly
145                 150                 155                 160

Val Val Val Ala Ile Val Asp Thr Gly Ile Asp Ala Asn His Pro Asp
                165                 170                 175

Leu Lys Gly Lys Val Ile Gly Trp Tyr Asp Ala Val Asn Gly Arg Ser
            180                 185                 190

Thr Pro Tyr Asp Asp Gln Gly His Gly Thr His Val Ala Gly Ile Val
        195                 200                 205

Ala Gly Thr Gly Ser Val Asn Ser Gln Tyr Ile Gly Val Ala Pro Gly
    210                 215                 220

Ala Lys Leu Val Gly Val Lys Val Leu Gly Ala Asp Gly Ser Gly Ser
225                 230                 235                 240

Val Ser Thr Ile Ile Ala Gly Val Asp Trp Val Val Gln Asn Lys Asp
                245                 250                 255

Lys Tyr Gly Ile Arg Val Ile Asn Leu Ser Leu Gly Ser Ser Gln Ser
            260                 265                 270

Ser Asp Gly Thr Asp Ser Leu Ser Gln Ala Val Asn Asn Ala Trp Asp
        275                 280                 285

Ala Gly Ile Val Cys Val Ala Ala Gly Asn Ser Gly Pro Asn Thr
    290                 295                 300

Tyr Thr Val Gly Ser Pro Ala Ala Ser Lys Val Ile Thr Val Gly
305                 310                 315                 320

Ala Val Asp Ser Asn Asp Asn Ile Ala Ser Phe Ser Arg Gly Pro
                325                 330                 335

Thr Ala Asp Gly Arg Leu Lys Pro Glu Val Val Ala Pro Gly Val Asp
            340                 345                 350

Ile Ile Ala Pro Arg Ala Ser Gly Thr Ser Met Gly Thr Pro Ile Asn
        355                 360                 365

Asp Tyr Tyr Thr Lys Ala Ser Gly Thr Ser Met Ala Thr Pro His Val
    370                 375                 380

Ser Gly Val Gly Ala Leu Ile Leu Gln Ala His Pro Ser Trp Thr Pro
385                 390                 395                 400

Asp Lys Val Lys Thr Ala Leu Ile Glu Thr Ala Asp Ile Val Ala Pro
                405                 410                 415

Lys Glu Ile Ala Asp Ile Ala Tyr Gly Ala Gly Arg Val Asn Val Tyr
            420                 425                 430

Lys Ala Ile Lys Tyr Asp Asp Tyr Ala Lys Leu Thr Phe Thr Gly Ser
        435                 440                 445

Val Ala Asp Lys Gly Ser Ala Thr His Thr Phe Asp Val Ser Gly Ala
    450                 455                 460

Thr Phe Val Thr Ala Thr Leu Tyr Trp Asp Thr Gly Ser Ser Asp Ile
465                 470                 475                 480
```

-continued

Asp Leu Tyr Leu Tyr Asp Pro Asn Gly Asn Glu Val Asp Tyr Ser Tyr
            485                 490                 495

Thr Ala Tyr Tyr Gly Phe Glu Lys Val Gly Tyr Tyr Asn Pro Thr Ala
            500                 505                 510

Gly Thr Trp Thr Val Lys Val Val Ser Tyr Lys Gly Ala Ala Asn Tyr
            515                 520                 525

Gln Val Asp Val Val Ser Asp Gly Ser Leu Ser Gln Ser Gly Gly Gly
            530                 535                 540

Asn Pro Asn Pro Asn Pro Asn Pro Asn Pro Thr Pro Thr Thr Asp Thr
545                 550                 555                 560

Gln Thr Phe Thr Gly Ser Val Asn Asp Tyr Trp Asp Thr Ser Asp Thr
            565                 570                 575

Phe Thr Met Asn Val Asn Ser Gly Ala Thr Lys Ile Thr Gly Asp Leu
            580                 585                 590

Thr Phe Asp Thr Ser Tyr Asn Asp Leu Asp Leu Tyr Leu Tyr Asp Pro
            595                 600                 605

Asn Gly Asn Leu Val Asp Arg Ser Thr Ser Ser Asn Ser Tyr Glu His
610                 615                 620

Val Glu Tyr Ala Asn Pro Ala Pro Gly Thr Trp Thr Phe Leu Val Tyr
625                 630                 635                 640

Ala Tyr Ser Thr Tyr Gly Trp Ala Asp Tyr Gln Leu Lys Ala Val Val
            645                 650                 655

Tyr Tyr Gly

<210> SEQ ID NO 13
<211> LENGTH: 28
<212> TYPE: DNA
<213> ORGANISM: Artificial Sequence
<220> FEATURE:
<223> OTHER INFORMATION: Synthetic

<400> SEQUENCE: 13
agagggatcc atgaaggggc tgaaagct                                        28

<210> SEQ ID NO 14
<211> LENGTH: 30
<212> TYPE: DNA
<213> ORGANISM: Artificial Sequence
<220> FEATURE:
<223> OTHER INFORMATION: Synthetic

<400> SEQUENCE: 14
agaggcatgc gctctagact ctgggagagt                                      30

<210> SEQ ID NO 15
<211> LENGTH: 1962
<212> TYPE: DNA
<213> ORGANISM: Artificial Sequence
<220> FEATURE:
<223> OTHER INFORMATION: Synthetic

<400> SEQUENCE: 15
atgaaggggc tgaaagctct catattagtg attttagttc taggtttggt agtagggagc      60
gtagcggcag ctccagagaa gaaagttgaa caagtaagaa atgttgagaa gaactatggt     120
ctgctaacgc caggactgtt cagaaaaatt caaaaattga atcctaacga ggaaatcagc     180
acagtaattg tatttgaaaa ccataggaa aaagaaattg cagtaagagt tcttgagtta     240
atgggtgcaa agttaggta tgtgtaccat attatacccg caatagctgc cgatcttaag     300

-continued

```
gttagagact tactagtcat ctcaggttta acaggggta aagctaagct ttcaggtgtt      360
aggtttatcc aggaagacta caaagttaca gtttcagcag aattagaagg actggatgag      420
tctgcagctc aagttatggc aacttacgtt tggaacttgg gatatgatgg ttctggaatc      480
acaataggaa taattgacac tggaattgac gcttctcatc cagatctcca aggaaaagta      540
attgggtggg tagattttgt caatggtagg agttatccat acgatgacca tggacatgga      600
actcatgtag cttcaatagc agctggtact ggagcagcaa gtaatggcaa gtacaaggga      660
atggctccag gagctaagct ggcgggaatt aaggttctag gtgccgatgg ttctggaagc      720
atatctacta taattaaggg agttgagtgg gccgttgata caaagataa gtacggaatt      780
aaggtcatta atctttctct tggttcaagc cagagctcag atggtactga cgctctaagt      840
caggctgtta atgcagcgtg ggatgctgga ttagttgttg tggttgccgc tggaaacagt      900
ggacctaaca agtatacaat cggttctcca gcagctgcaa gcaaagttat tacagttgga      960
gccgttgaca gtatgatgt tataacaagc ttctcaagca gagggccaac tgcagacggc     1020
aggcttaagc ctgaggttgt tgctccagga aactggataa ttgctgccag agcaagtgga     1080
actagcatgg gtcaaccaat taatgactat tacacagcac ctcctgggac atcaatggca     1140
actcctcacg tagctggtat tgcagccctc ttgctccaag cacacccgag ctggactcca     1200
gacaaagtaa aaacagccct catagaaact gctgatatcg taaagccaga tgaaatagcc     1260
gatatagcct acggtgcagg tagggttaat gcatacaagg ctataaacta cgataactat     1320
gcaaagctag tgttcactgg atatgttgcc aacaaaggca gccaaactca ccagttcgtt     1380
attagcggag cttcgttcgt aactgccaca ttatactggg acaatgccaa tagcgacctt     1440
gatctttacc tctacgatcc caatggaaac caggttgact actcttacac cgcctactat     1500
ggattcgaaa aggttggtta ttacaaccca actgatggaa catggacaat taaggttgta     1560
agctacagcg gaagtgcaaa ctatcaagta gatgtggtaa gtgatggttc cctttcacag     1620
cctggaagtt caccatctcc acaaccagaa ccaacagtag acgcaaagac gttccaagga     1680
tccgatcact actactatga caggagcgac acctttacaa tgaccgttaa ctctggggct     1740
acaaagatta ctggagacct agtgtttgac acaagctacc atgatcttga cctttacctc     1800
tacgatccta accagaagct tgtagataga tcggagagtc ccaacagcta cgaaacgta      1860
gaatacttaa cccccgcccc aggaacctgg tacttcctag tatatgccta ctacacttac     1920
ggttgggctt actacgagct gacggctaaa gtttattatg gc                        1962
```

<210> SEQ ID NO 16
<211> LENGTH: 654
<212> TYPE: PRT
<213> ORGANISM: Pyrococcus furiosus

<400> SEQUENCE: 16

```
Met Lys Gly Leu Lys Ala Leu Ile Leu Val Ile Leu Val Leu Gly Leu
1               5                   10                  15

Val Val Gly Ser Val Ala Ala Ala Pro Glu Lys Lys Val Glu Gln Val
                20                  25                  30

Arg Asn Val Glu Lys Asn Tyr Gly Leu Leu Thr Pro Gly Leu Phe Arg
            35                  40                  45

Lys Ile Gln Lys Leu Asn Pro Asn Glu Glu Ile Ser Thr Val Ile Val
        50                  55                  60

Phe Glu Asn His Arg Glu Lys Glu Ile Ala Val Arg Val Leu Glu Leu
65                  70                  75                  80
```

```
Met Gly Ala Lys Val Arg Tyr Val Tyr His Ile Ile Pro Ala Ile Ala
                85                  90                  95
Ala Asp Leu Lys Val Arg Asp Leu Leu Val Ile Ser Gly Leu Thr Gly
                100                 105                 110
Gly Lys Ala Lys Leu Ser Gly Val Arg Phe Ile Gln Glu Asp Tyr Lys
                115                 120                 125
Val Thr Val Ser Ala Glu Leu Glu Gly Leu Asp Glu Ser Ala Ala Gln
    130                 135                 140
Val Met Ala Thr Tyr Val Trp Asn Leu Gly Tyr Asp Gly Ser Gly Ile
145                 150                 155                 160
Thr Ile Gly Ile Ile Asp Thr Gly Ile Asp Ala Ser His Pro Asp Leu
                165                 170                 175
Gln Gly Lys Val Ile Gly Trp Val Asp Phe Val Asn Gly Arg Ser Tyr
                180                 185                 190
Pro Tyr Asp Asp His Gly His Gly Thr His Val Ala Ser Ile Ala Ala
                195                 200                 205
Gly Thr Gly Ala Ala Ser Asn Gly Lys Tyr Lys Gly Met Ala Pro Gly
    210                 215                 220
Ala Lys Leu Ala Gly Ile Lys Val Leu Gly Ala Asp Gly Ser Gly Ser
225                 230                 235                 240
Ile Ser Thr Ile Ile Lys Gly Val Glu Trp Ala Val Asp Asn Lys Asp
                245                 250                 255
Lys Tyr Gly Ile Lys Val Ile Asn Leu Ser Leu Gly Ser Ser Gln Ser
                260                 265                 270
Ser Asp Gly Thr Asp Ala Leu Ser Gln Ala Val Asn Ala Ala Trp Asp
    275                 280                 285
Ala Gly Leu Val Val Val Ala Ala Gly Asn Ser Gly Pro Asn Lys
    290                 295                 300
Tyr Thr Ile Gly Ser Pro Ala Ala Ala Ser Lys Val Ile Thr Val Gly
305                 310                 315                 320
Ala Val Asp Lys Tyr Asp Val Ile Thr Ser Phe Ser Ser Arg Gly Pro
                325                 330                 335
Thr Ala Asp Gly Arg Leu Lys Pro Glu Val Val Ala Pro Gly Asn Trp
                340                 345                 350
Ile Ile Ala Ala Arg Ala Ser Gly Thr Ser Met Gly Gln Pro Ile Asn
                355                 360                 365
Asp Tyr Tyr Thr Ala Ala Pro Gly Thr Ser Met Ala Thr Pro His Val
    370                 375                 380
Ala Gly Ile Ala Ala Leu Leu Leu Gln Ala His Pro Ser Trp Thr Pro
385                 390                 395                 400
Asp Lys Val Lys Thr Ala Leu Ile Glu Thr Ala Asp Ile Val Lys Pro
                405                 410                 415
Asp Glu Ile Ala Asp Ile Ala Tyr Gly Ala Gly Arg Val Asn Ala Tyr
                420                 425                 430
Lys Ala Ile Asn Tyr Asp Asn Tyr Ala Lys Leu Val Phe Thr Gly Tyr
                435                 440                 445
Val Ala Asn Lys Gly Ser Gln Thr His Gln Phe Val Ile Ser Gly Ala
    450                 455                 460
Ser Phe Val Thr Ala Thr Leu Tyr Trp Asp Asn Ala Asn Ser Asp Leu
465                 470                 475                 480
Asp Leu Tyr Leu Tyr Asp Pro Asn Gly Asn Gln Val Asp Tyr Ser Tyr
                485                 490                 495
Thr Ala Tyr Tyr Gly Phe Glu Lys Val Gly Tyr Tyr Asn Pro Thr Asp
```

-continued

```
                      500                 505                 510
Gly Thr Trp Thr Ile Lys Val Val Ser Tyr Ser Gly Ser Ala Asn Tyr
            515                 520                 525
Gln Val Asp Val Val Ser Asp Gly Ser Leu Ser Gln Pro Gly Ser Ser
        530                 535                 540
Pro Ser Pro Gln Pro Glu Pro Thr Val Asp Ala Lys Thr Phe Gln Gly
545                 550                 555                 560
Ser Asp His Tyr Tyr Tyr Asp Arg Ser Asp Thr Phe Thr Met Thr Val
                565                 570                 575
Asn Ser Gly Ala Thr Lys Ile Thr Gly Asp Leu Val Phe Asp Thr Ser
            580                 585                 590
Tyr His Asp Leu Asp Leu Tyr Leu Tyr Asp Pro Asn Gln Lys Leu Val
        595                 600                 605
Asp Arg Ser Glu Ser Pro Asn Ser Tyr Glu His Val Glu Tyr Leu Thr
610                 615                 620
Pro Ala Pro Gly Thr Trp Tyr Phe Leu Val Tyr Ala Tyr Tyr Thr Tyr
625                 630                 635                 640
Gly Trp Ala Tyr Tyr Glu Leu Thr Ala Lys Val Tyr Tyr Gly
                645                 650
```

<210> SEQ ID NO 17
<211> LENGTH: 25
<212> TYPE: DNA
<213> ORGANISM: Artificial Sequence
<220> FEATURE:
<223> OTHER INFORMATION: Synthetic

<400> SEQUENCE: 17
tctgaattcg ttctttctg tatgg                                    25

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
tgtactgctg gatccggcag                                         20

<210> SEQ ID NO 19
<211> LENGTH: 30
<212> TYPE: DNA
<213> ORGANISM: Artificial Sequence
<220> FEATURE:
<223> OTHER INFORMATION: Synthetic

<400> SEQUENCE: 19
agaggcatgc gtatccatca gatttttgag                              30

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
agtgaacgga tacttggaac                                         20

<210> SEQ ID NO 21

```
<211> LENGTH: 20
<212> TYPE: DNA
<213> ORGANISM: Artificial Sequence
<220> FEATURE:
<223> OTHER INFORMATION: Synthetic

<400> SEQUENCE: 21
gttccaagta tccgttcact                                               20

<210> SEQ ID NO 22
<211> LENGTH: 12
<212> TYPE: PRT
<213> ORGANISM: Pyrococcus furiosus

<400> SEQUENCE: 22

Ala Glu Leu Glu Gly Leu Asp Glu Ser Ala Ala Gln
 1               5                  10

<210> SEQ ID NO 23
<211> LENGTH: 24
<212> TYPE: DNA
<213> ORGANISM: Artificial Sequence
<220> FEATURE:
<223> OTHER INFORMATION: Synthetic

<400> SEQUENCE: 23
tcatggatcc accctctcct ttta                                          24

<210> SEQ ID NO 24
<211> LENGTH: 46
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(25)
<223> OTHER INFORMATION: n at postions 20-25 is a, c, g, or t.

<400> SEQUENCE: 24
gtctgcgcag gctgccggan nnnnnatgaa ggggctgaaa gctctc                  46

<210> SEQ ID NO 25
<211> LENGTH: 49
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(27)
<223> OTHER INFORMATION: n at postions 22-27 is a, c, g, or t.

<400> SEQUENCE: 25
gagagctttc agcccttca tnnnnnntcc ggcagcctgc gcagacatg                49

<210> SEQ ID NO 26
<211> LENGTH: 27
<212> TYPE: DNA
<213> ORGANISM: Artificial Sequence
<220> FEATURE:
<223> OTHER INFORMATION: Synthetic

<400> SEQUENCE: 26 agaggggat ccgtgagaag caaaaaa                                        27

<210> SEQ ID NO 27
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 27
gatgactagt aagtctctaa                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
aagcctgagg ttgttgctcc                                              20

<210> SEQ ID NO 29
<211> LENGTH: 29
<212> TYPE: DNA
<213> ORGANISM: Artificial Sequence
<220> FEATURE:
<223> OTHER INFORMATION: Synthetic

<400> SEQUENCE: 29
gggcatgctc atgaacttcc aggctgtga                                    29

<210> SEQ ID NO 30
<211> LENGTH: 4
<212> TYPE: PRT
<213> ORGANISM: Artificial Sequence
<220> FEATURE:
<223> OTHER INFORMATION: Synthetic

<400> SEQUENCE: 30

Ala Gly Gly Asn
1

<210> SEQ ID NO 31
<211> LENGTH: 382
<212> TYPE: PRT
<213> ORGANISM: Bacillus subtilis

<400> SEQUENCE: 31

Met Arg Gly Lys Lys Val Trp Ile Ser Leu Leu Phe Ala Leu Ala Leu
1               5                   10                  15

Ile Phe Thr Met Ala Phe Gly Ser Thr Ser Ser Ala Gln Ala Ala Gly
                20                  25                  30

Lys Ser Asn Gly Glu Lys Lys Tyr Ile Val Gly Phe Lys Gln Thr Met
            35                  40                  45

Ser Thr Met Ser Ala Ala Lys Lys Lys Asp Val Ile Ser Glu Lys Gly
        50                  55                  60

Gly Lys Val Gln Lys Gln Phe Lys Tyr Val Asp Ala Ala Ser Ala Thr
65                  70                  75                  80

Leu Asn Glu Lys Ala Val Lys Glu Leu Lys Lys Asp Pro Ser Val Ala
                85                  90                  95

Tyr Val Glu Glu Asp His Val Ala His Ala Tyr Ala Gln Ser Val Pro
                100                 105                 110

Tyr Gly Val Ser Gln Ile Lys Ala Pro Ala Leu His Ser Gln Gly Tyr
            115                 120                 125
```

```
Thr Gly Ser Asn Val Lys Val Ala Val Ile Asp Ser Gly Ile Asp Ser
        130                 135                 140
Ser His Pro Asp Leu Lys Val Ala Gly Gly Ala Ser Met Val Pro Ser
145                 150                 155                 160
Glu Thr Asn Pro Phe Gln Asp Asn Asn Ser His Gly Thr His Val Ala
                165                 170                 175
Gly Thr Val Ala Ala Leu Asn Asn Ser Ile Gly Val Leu Gly Val Ala
            180                 185                 190
Pro Ser Ala Ser Leu Tyr Ala Val Lys Val Leu Gly Ala Asp Gly Ser
        195                 200                 205
Gly Gln Tyr Ser Trp Ile Ile Asn Gly Ile Glu Trp Ala Ile Ala Asn
    210                 215                 220
Asn Met Asp Val Ile Asn Met Ser Leu Gly Gly Pro Ser Gly Ser Ala
225                 230                 235                 240
Ala Leu Lys Ala Ala Val Asp Lys Ala Val Ala Ser Gly Val Val Val
                245                 250                 255
Val Ala Ala Ala Gly Asn Glu Gly Thr Ser Gly Ser Ser Ser Thr Val
            260                 265                 270
Gly Tyr Pro Gly Lys Tyr Pro Ser Val Ile Ala Val Gly Ala Val Asp
        275                 280                 285
Ser Ser Asn Gln Arg Ala Ser Phe Ser Ser Val Gly Pro Glu Leu Asp
    290                 295                 300
Val Met Ala Pro Gly Val Ser Ile Gln Ser Thr Leu Pro Gly Asn Lys
305                 310                 315                 320
Tyr Gly Ala Tyr Asn Gly Thr Ser Met Ala Ser Pro His Val Ala Gly
                325                 330                 335
Ala Ala Ala Leu Ile Leu Ser Lys His Pro Asn Trp Thr Asn Thr Gln
            340                 345                 350
Val Arg Ser Ser Leu Glu Asn Thr Thr Thr Lys Leu Gly Asp Ser Phe
        355                 360                 365
Tyr Tyr Gly Lys Gly Leu Ile Asn Val Gln Ala Ala Ala Gln
    370                 375                 380

<210> SEQ ID NO 32
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Residue 1 is modified by a succinyl group.
<220> FEATURE:
<221> NAME/KEY: misc_feature
<223> OTHER INFORMATION: Residue 4 is modified by a 4-methylcoumarin-7-
      amide group.

<400> SEQUENCE: 32

Leu Leu Val Tyr
1

<210> SEQ ID NO 33
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Residue 1 is modified by a succinyl group.
<220> FEATURE:
```

```
<221> NAME/KEY: misc_feature
<223> OTHER INFORMATION: Residue 4 is modified by a p-nitroaniline
      group.

<400> SEQUENCE: 33

Ala Ala Pro Phe
1
```